United States Patent [19]

Crounse et al.

[11] 3,993,658

[45] Nov. 23, 1976

[54] THIAZOLIDINYLIDENE-ISOINDOLINES

[75] Inventors: Nathan N. Crounse; Nicholas A. Ambrosiano, both of Cincinnati, Ohio

[73] Assignee: Sterling Drug Inc., New York, N.Y.

[22] Filed: Apr. 3, 1975

[21] Appl. No.: 564,725

Related U.S. Application Data

[63] Continuation-in-part of Ser. No. 308,163, Nov. 20, 1972, Pat. No. 3,919,235.

[52] U.S. Cl. .................. 260/306.7 R; 260/306.7 T
[51] Int. Cl.² ........................................ C07D 417/14
[58] Field of Search ............... 260/306.7 R, 306.7 T

[56] References Cited
UNITED STATES PATENTS

| 2,388,963 | 11/1945 | Fry et al. | 260/306.7 R |
| 2,875,053 | 2/1959 | Minsk | 260/306.7 T |
| 3,919,235 | 11/1975 | Crounse et al. | 260/270 |

Primary Examiner—R. Gallagher
Attorney, Agent, or Firm—Lynn T. Fletcher; B. Woodrow Wyatt

[57] ABSTRACT

This invention relates to novel compounds of the isoindolenine series. More particularly, the present invention relates to certain novel 1-imino-3-(4-imino-5-thiazolidinylidene)isoindolines, 1-imino-3-(4-imino-2-thiazolin-5-ylidene)isoindolines, water-insoluble pigments prepared therefrom, and to methods for their preparation.

7 Claims, No Drawings

THIAZOLIDINYLIDENE-ISOINDOLINES

This application is a continuation-in-part of our prior copending application Ser. No. 308,163, filed Nov. 20, 1972, now U.S. Pat. No. 3,919,235, issued Nov. 11, 1975.

The invention described herein relates to new and useful compounds classified in the art of chemistry as 1-imino-3-(4-imino-5-thiazolidinylidene)isoindolines and 1-imino-3-(4-imino-2-thiazolin-5-ylidene)isoindolines, to valuable metal chelate pigments derived therefrom and to intermediates and processes for obtaining them.

The invention sought to be patented, in a first composition of matter aspect, resides in the novel metal chelate pigments of the formula

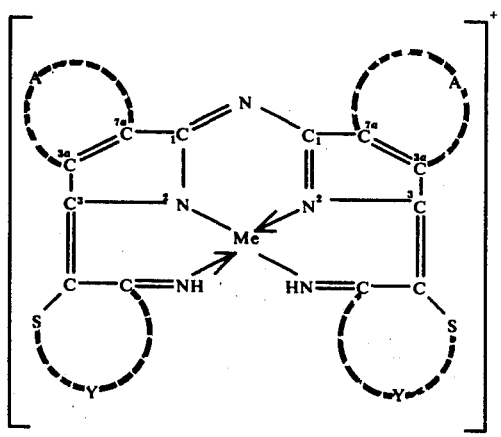

Formula I and $R_3$ are the same or different and are selected from the class consisting of hydrogen, alkyl having 1 to 3 carbon atoms, alkoxy having 1 to 3 carbon atoms, halo, trifluoromethyl, phenyl and phenyl substituted by alkyl having one to three carbon atoms, alkoxy having 1 to 3 carbon atoms and halogen; Me is a metal selected from the class consisting of copper, cobalt and nickel; Y is a divalent radical combining with the —S—C—C— portion of the molecule to form a five-membered heterocyclic ring having the same orientation as a thiazole ring and selected from the group consisting of

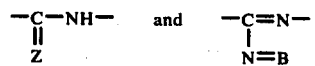

in which Z is NH, O or S, and N=B is lower-alkylamino, di-lower-alkylamino, piperidino, pyrrolidino, morpholino, phenylamino, (lower-alkyl)-(phenyl)amino, phenyl-lower-alkylamino or (lower-alkyl)-(-lower-alkyl-)amino; and An is an anion.

Particularly preferred embodiments of the above-described composition of matter aspect are as follows:

a. Compounds of Formula I wherein A is $$-C=C-C=C-$$
with substituents $R$, $R_1$, $R_2$, $R_3$ and Y is

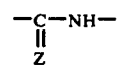

of the formula

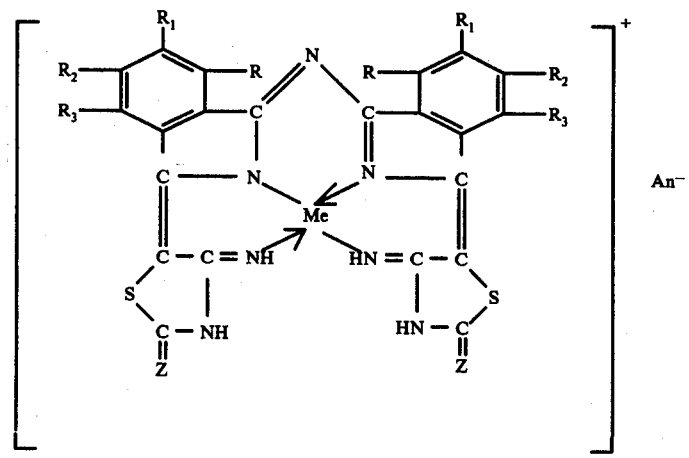

Formula II in which Me, R, $R_1$, $R_2$, $R_3$, Z and An each have the same respective meanings indicated in relation to Formula I.

b. Compounds of Formula I wherein A is $$-C=C-C=C-$$
with substituents $R$, $R_1$, $R_2$, $R_3$ and Y is wherein A is a divalent radical combining with the —C=C— portion of the molecule to which it is attached to form a six-membered carbocyclic ring and is selected from the class having the formulas

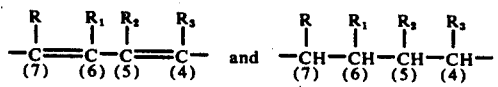

where in each instance C(7) and C(4) are bonded to C(7a) and C(3a) respectively, and in which R, $R_1$, $R_2$ of the formula 

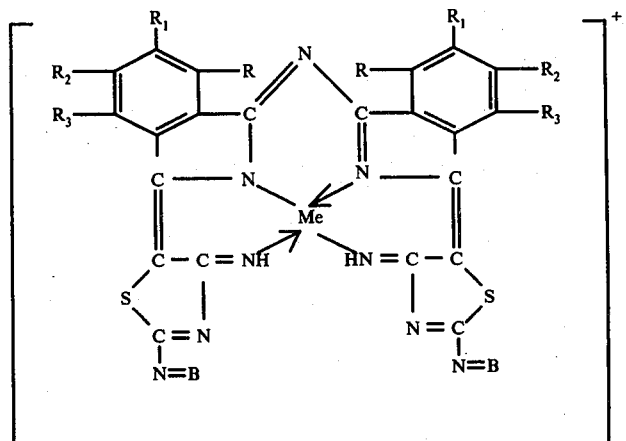

Formula III in which Me, R, $R_1$, $R_2$, $R_3$, N=B and An each have the same respective meanings indicated in relation to Formula I.

c. Compounds of Formula I wherein A is

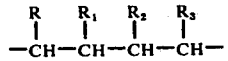

and Y is

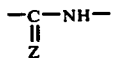

of the formula in which Me, R, $R_1$, $R_2$, $R_3$ and Z each have the same respective meanings indicated in relation to Formula I.

d. Compounds of Formula I wherein A is

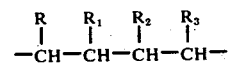

and Y is $$-C{\equiv}N- \\ N{=}B$$

of the formula

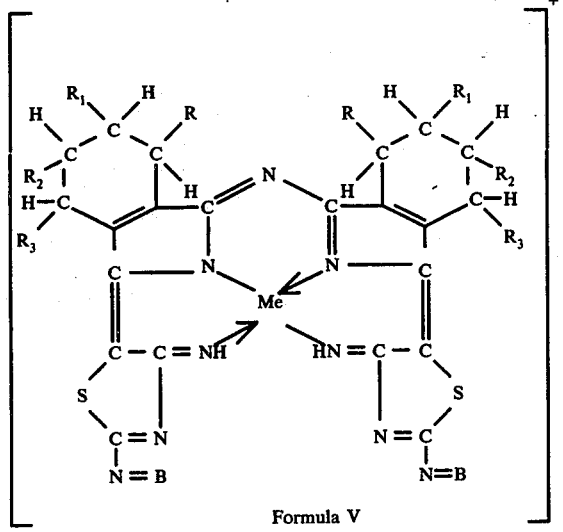

Formula V

Formula IV in which Me, R, $R_1$, $R_2$, $R_3$ and N=B each have the same respective meanings indicated in relation to Formula I.

The compounds of Formula I (and Formulas II, III, IV and V) which are metal chelates of 1-imino-3-(4-imino-5-thiazolidinylidene)isoindolines and 1-imino-3-(4-imino-2-thiazolin-5-ylidene)isoindolines, are water-insoluble pigments, red in shade, and have improved light stability. They are useful for coloring natural fibers, synthetic fiber-forming material and cellulosic materials such as threads, sheets, fibers, filaments, textile fabrics and the like, as well as in the manufacture of paper, varnishes, inks, coatings and plastics. Because of their excellent light-fastness, the pigments of this invention are particularly suitable for the preparation of coatings that are designed for outdoor exposure such as automotive finishes.

The invention sought to be patented, in a second composition of matter aspect, resides in the novel 1-imino-3-(4-imino-5-thiazolidinylidene)isoindolines and 1-imino-3-(4-imino-2-thiazolin-5-ylidene)isoindolines represented by the formula

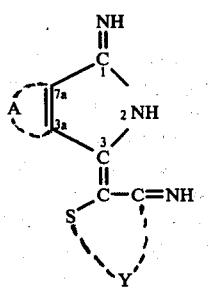

wherein A is a divalent radical combining with the —C=C— portion of the molecule to which it is attached to form a six-membered carbocyclic ring and is selected from the class having the formulas

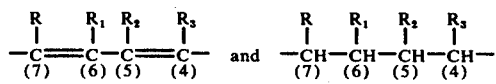

where in each instance C(7) and C(4) are bonded to C(7a) and C(3a) respectively, and in which R, $R_1$, $R_2$ and $R_3$ are the same or different and are selected from the class consisting of hydrogen, alkyl having one to three carbon atoms, alkoxy having 1 to 3 carbon atoms, halo, trifluoromethyl, phenyl and phenyl substituted by alkyl having 1 to 3 carbon atoms, alkoxy having one to three carbon atoms and halogen; and Y is a divalent radical combining with the —S—C—C— portion of the molecule to form a five-membered heterocyclic ring having the same orientation as a thiazole ring and selected from the group consisting of

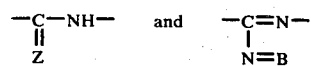

in which Z is NH, O or S, and N=B is lower-alkylamino, di-lower-alkylamino, piperidino, pyrrolidino, morpholino, phenylamino (lower-alkyl)-(phenyl)amino, phenyl-lower-alkylamino or (lower-alkyl)-(phenyl-lower-alkyl)amino.

Particularly preferred embodiments in accordance with its second composition of matter aspect are as follows:

1. The novel 1-imino-3-(4-imino-5-thiazolidinylidene)isoindolines of Formula VI wherein A is

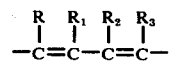

and Y is

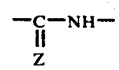

of the formula

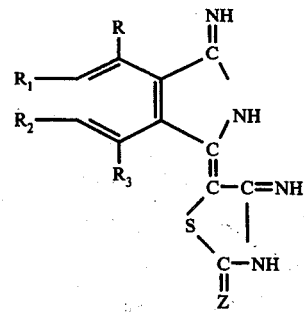

Formula VII in which R, $R_1$, $R_2$, $R_3$ and Z each have the same respective meanings indicated in relation to Formula VI.

2. The novel 1-imino-3-(4-imino-2-thiazolin-5-ylidene)isoindolines of Formula VI wherein A is

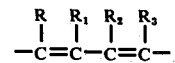

and Y is

of the formula

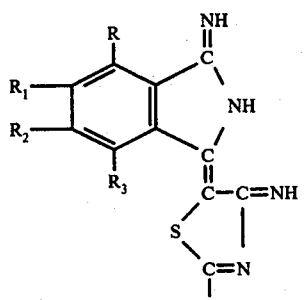

Formula VIII in which R, R₁, R₂, R₃ and N=B each have the same respective meanings given in Formula VI.

3. The novel 1-imino-3-(4-imino-5-thiazolidinylidene)isoindolines of Formula VI wherein A is

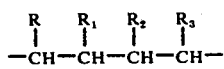

and Y is

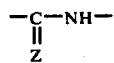

of the formula

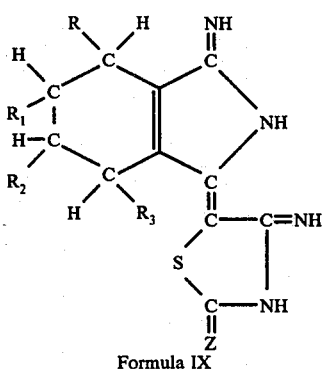

Formula IX in which R, R₁, R₂, R₃ and Z each have the same respective meanings given in Formula VI.

4. The novel 1-imino-3-(4-imino-2-thiazolin-5-ylidene)isoindolines of Formula VI wherein A is

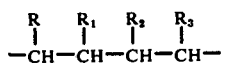

and Y is

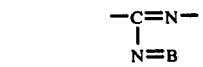

of the formula

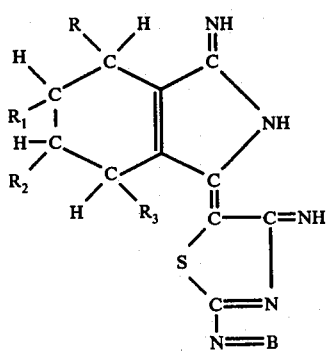

Formula X in which R, R₁, R₂, R₃ and N=B each have the same respective meanings given in Formula VI.

It will, of course, be understood by those skilled in the art that the compounds of this invention, both final products and intermediates, may exist and may be represented in any one of several tautomeric forms. However, structural determinations lead to the conclusion that the forms depicted by the structural formulas and as named are the most likely under ordinary conditions.

In the first of its process aspects, the invention sought to be patented resides in the process which comprises interacting approximately two molecular equivalents of a compound of the formula

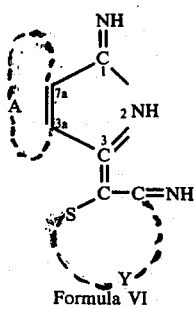

Formula VI or preferably the zinc halide adduct thereof with approximately one molecular equivalent of a metal salt, MeAn₂, wherein A, Me, Y and An each have the same respective meanings given in relation to Formula I and Formula VI above.

In a second process aspect, the invention sought to be patented resides in the process for preparing the novel 1-imino-3-(4-imino-5-thiazolidinylidene)isoindolines and 1-imino-3-(4-imino-2-thiazolin-5-ylidene)isoindolines of Formula VI which comprises interacting in approximately equimolecular proportions a compound of the formula

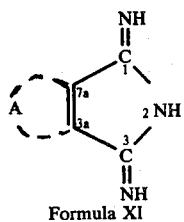

Formula XI and a compound of the formula

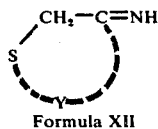

Formula XII wherein A and Y each have the same respective meanings given in relation to Formula VI above.

As used throughout, the term "halogen" includes bromine, chlorine, fluorine and iodine.

As used herein the term "alkyl having 1 to 3 carbon atoms" includes saturated straight- or branched-chain aliphatic radicals represented by, for example, methyl, ethyl, propyl and isopropyl.

Similarly, the term "alkoxy having 1 to 3 carbon atoms" includes straight- or branched-chain aliphatic groups attached to the oxygen atom. Included in this term are, for example, methoxy, ethoxy, propoxy and isopropoxy.

In the above general formula, the radical N=B includes: lower-alkylamino; di-lower-alkylamino; saturated N-heterocyclic groups, such as piperidino, pyrrolidino, morpholino, and lower-alkylated derivatives thereof (for example, 2-methylpiperidino, 3-ethylpyrrolidino, 3-methylmorpholino and the like); phenylamino: (lower-alkyl)-(phenyl)amino; phenyl-lower-alkylamino or (lower-alkyl)-(phenyl-lower-alkyl)amino. The term lower-alkyl includes alkyl radicals containing from 1 to 6 carbon atoms which can be straight or branched. Included in the lower-alkylamino groups are, for example, methylamino, ethylamino, propylamino, isopropylamino, butylamino, tert.-butylamino, pentylamino and n-hexylamino. In the di-lower-alkylamino radicals the lower-alkyl groups can be the same or different and thus N=B, when it represents a di-lower-alkylamino radical, includes such groups as dimethylamino, diethylamino, ethylmethylamino, dipropylamino, dibutylamino, dipentylamino and dihexylamino.

When N=B represents a phenyl-lower-alkylamino group there are included such groups as benzylamino, phenylethylamino, phenylpentylamino; and the like. When N=B represents a (lower-alkyl)-(phenyl)amino group there are included such groups as (methyl)-(phenyl)amino, $N(CH_3)(C_6H_5)$; (ethyl)-(phenyl)amino, $N(C_2H_5)(C_6H_5)$; (isopropyl)-(phenyl)amino, $N(i-C_3H_7)(C_6H_5)$; (butyl)-(phenyl)amino, $N(C_4H_9)(C_6H_5)$; (hexyl)-(phenyl)amino, $N(C_6H_{13})(C_6H_5)$; and the like. In the preferred types of (lower-alkyl)-(phenyl)amino groups, the lower-alkyl groups have from one to six carbon atoms. When representing (lower-alkyl)-(phenyl-lower-alkyl)amino, N=B includes (methyl)-(benzyl)amino, $N(CH_3)(C_6H_5CH_2)$; (ethyl)-(phenylethyl)amino, $N(C_2H_5)(C_6H_5CH_2CH_2)$; (propyl)-(benzyl)amino, $N(C_3H_7)(C_6H_5CH_2)$; (butyl)-(phenylethyl)amino, $N(C_4H_9)(C_6H_5CH_2CH_2)$; and the like. In the preferred types of (lower-alkyl)-(phenyl-lower-alkyl)amino groups, the lower-alkyl groups have from 1 to 6 carbon atoms and the alkylene radicals of the phenyl-lower-alkyl groups have from 1 to 4 carbon atoms.

The term anion, as used herein, means a monovalent inorganic or organic anion. The choice of an anion is not critical in the operation of the preparative processes nor is the identity of the anion a critical feature of the claimed products. Accordingly, by way of illustration and without limitation thereto, the anion can be, for example, bromide, chloride, iodide, hydroxide, nitrate, acetate, p-toluenesulfonate and the like. Particularly preferred anions are bromide and chloride because of the lower cost and greater availability of the nickel, copper or cobalt salts bearing those anions.

The metal chelate pigments of this invention are useful for coloring or printing paper and cardboard as well as for coloring paper pulps. They are also useful for coloring and printing textile materials made from natural fibers, such as wool, cotton or linen, those made from semi-synthetic fibers, such as regenerated cellulose as represented by rayon or viscose or those made from synthetic fibers, such as polyaddition, polycondensation or polymerization compounds. Such colorings or printings can be carried out with the subject pigments in accordance with the usual pigment coloring and printing processes.

The metal chelate pigments of this invention are also useful for incorporation into lacquers and films of various constitution, for example, those made from cellulose acetate, cellulose propionate, polyvinyl chloride, polyethylene, polypropylene, polyamides, polyesters or alkyd resins. In addition the subject compounds are suitable for coloring natural or synthetic resins, for example acrylic resins, epoxy resins, polyester resins, vinyl resins, polystyrene resins or alkyd resins. When dispersed in a clear coating composition vehicle with the incorporation of a small amount of flake aluminum and the compositions coated and cured on steel test panels, the subject pigments show excellent transparency, cleanliness and good intensity.

The metal chelate pigments of this invention are characterized by excellent light-fastness both under accelerated exposure evaluations and under prolonged outdoor exposure. Thus, when the subject pigments suspended in cured acrylic resin dispersion coated on foil-covered paper are exposed to carbon arc radiation, there is no loss in color value of the pigments after 300 hours of continuous exposure. Moreover, when steel plates coated with a cured acrylic resin dispersion of the subject pigments were exposed for twelve months in Florida, there was substantially no loss in color value or any indication of darkening.

The best mode contemplated by the inventors of carrying out this invention will now be described as to enable any person skilled in the art to which it pertains to make and use the same.

Generally speaking, the novel metal chelate pigments of Formula I are conveniently obtained by interacting approximately two molecular equivalents of the appropriate 1-imino-3-(4-imino-5-thiazolidinylidene)isoindoline or 1-imino-3-(4-imino-2-thiazolin-5-ylidene)isoindoline of Formula VI with one molecular equivalent of a metal salt, MeAn$_2$, wherein Me and An have the same meanings given hereinabove. The reaction is preferably carried out at a temperature between about 0° and 100° C in either an aprotic or protic solvent. Aprotic solvents suitable for the reaction are, for example, dimethylformamide, dimethylsulfoxide and hexamethylphosphoramide. Among protic solvents useful for this reaction are, for example, water; lower-aliphatic alcohols, for instance methanol, ethyl alcohol, isopropyl alcohol, etc.; and ether glycols, for instance, 2methoxyethanol, 2-ethoxyethanol, etc.

An alternate and preferred procedure for preparing the metal chelates of Formula I is carried out by interacting approximately two molecular equivalents of a zinc halide adduct of the appropriate 1-imino-3-(4-imino-5-thiazolidinylidene)isoindoline or 1-imino-3-(4-imino-2-thiazolin-5-ylidene)isoindoline of Formula VI with one molecular equivalent of a metal salt, MeAn$_2$, wherein Me and An have the same meanings given hereinabove. The reaction using the zinc halide adduct is preferably carried out at a temperature between about 0° and 100° C in an aprotic solvent, for example, dimethylformamide, dimethylsulfoxide, hexamethylphosphoramide, etc. The requisite zinc halide adduct is readily obtained by treatment of the appropriate 1-imino-3-(4-imino-5-thiazolidinylidene)isoindoline or 1-imino-3-(4-imino-2-thiazolin-2-ylidene)isoindoline with a solution of the zinc halide in an aprotic solvent, for example, dimethylformamide. Although the adduct, which is initially obtained as a solid suspended in the aprotic solvent may be subjected without isolation to interaction with the chelating metal salt, we generally prefer to separate the product by filtration prior to its use for forming the metal chelate pigment. Particularly preferred zinc halides for preparation of the adduct are zinc chloride and zinc bromide and particularly preferred temperature for the preparation of the metal chelates, either directly or by way of the zinc halide adduct, is at a temperature between about 15° and 50° C.

We have also found that the novel metal chelate pigments of Formula I are obtained by first interacting approximately two molecular equivalents of the appropriate 1,3-diiminoisoindoline with one molecular equivalent of a metal salt, MeAn$_2$, followed by the addition of approximately two molecular equivalents of the appropriate iminothiazolidine or iminothiazoline. The same general conditions of reaction, that is, temperature and solvent system described for the preparative methods described above are also applicable to this synthetic approach.

The metal chelate pigments of this invention which bear either of the preferred anions, bromide or chloride, are, of course, obtained by direct chelation of the appropriate compound of Formulas VII, VIII, IX or X with the appropriate metal (II) bromide or chloride. However, we have found that corresponding metal chelate pigments bearing hydroxide as the anion are obtained by employing a metal (II) salt in which the anion is organic in nature. For example, when the appropriate 1-imino-3-(4-imino-5-thiazolidinylidene)isoindoline or 1-imino-3-(4-imino-2-thiazolin- 5-ylidene)isoindoline is subjected to interaction with the appropriate hydrated metal (II) p-toluenesulfonate in the presence of dimethylformamide, the anion obtained is hydroxide. The same result is also obtained by anion exchange. Thus, when the corresponding metal chelate pigment bearing a halide as the anion is heated for several hours in the presence of aqueous methanesulfonic acid, the halide is replaced by hydroxide. On the other hand, for reasons that are not completely understood, we have found that heating the same metal chelate pigment bearing halide as the anion with aqueous p-toluenesulfonic acid for several hours, yields the corresponding metal chelate pigment bearing a p-toluenesufonate anion.

The novel 1-imino-3-(4-imino-5-thiazolidinylidene)isoindolines and 1-imino-3-(4-imino-2-thiazolin-5-ylidene)isoindolines represented by Formula VI, which are used to prepare the metal chelate pigments of Formula I are readily prepared by the condensation of the appropriate 1,3-diiminoisoindoline through one of the imino moieties with the loss of ammonia at the site of the active methylene moiety of the appropriate 4-iminothiazolidine or 4-imino-2-thiazoline. The iminothiazolidines and iminothiazolines used in the preparation are generally unstable in the free-base form and are preferably employed in the form of their acid addition salts, for example, the hydrochloride, benzenesulfonate, etc. The reaction proceeds smoothly at reflux in a lower-aliphatic alcohol such as methanol and is preferably carried out under an atmosphere of nitrogen. When the acid addition salt is used in the reaction, the resultant 1-imino-3-(4-imino-5-thiazolidinylidene)isoindoline or 1-imino-3-(4-imino-2-thiazolin-5-ylidene)isoindoline separates in the form of an acid addition salt which is converted to its free-base form by treatment with a slight excess of a base, such as triethylamine. Alternatively, the acid addition salt form of the iminothiazolidine or iminothiazoline can be converted initially to the free-base form in situ by the addition of a stoichiometric quantity of a base to the reaction mixture prior to the addition of the 1,3-diiminoisoindoline.

The 1,3-diiminoisoindolines of Formula XI required for the preparation of the novel 1-imino-3-(4-imino-5-thiazolidinylidene)isoindolines and the 1-imino-3-(4-imino-2-thiazolin-5-ylidene)isoindolines of Formula VI are a known class of compounds readily obtained by procedures well-known in the prior art [cf. e.g. (1) Angew. Chem. 68, 133 (1956); (2) J. Chem. Soc. 3525 (1955); (3) Brit. Pat. Specification 698,049]. For example, an appropriate phthalonitrile is interacted with ammonia or with a substance which gives off ammonia under the reaction conditions, for instance, urea to obtain the corresponding 1,3-diiminoisoindoline. For example, the following 1,3-diiminoisoindolines of Formula XI are useful starting materials for preparing both the 1-imino-3-(4-imino-5-thiazolidinylidene)isoindolines and the 1-imino-3-(4-imino-2-thiazolin-5-ylidene)isoindolines represented by Formula VI above. Those intermediates in the following list whose physical properties and/or preparation are described in the above-mentioned references, (1), (2) or (3), are so indicated.

1,3-Diiminoisoindoline, mp 180°–182° C (dec) (1)
4,5,6,7-Tetrahydro- 1,3-diiminoisoindoline, mp 177°–180° C (dec) (2)
5-Methyl-1,3-diiminoisoindoline, mp 189°–190° C (dec) (3)

4,5-Dimethyl-1,3-diiminoisoindoline
5,6-Dimethyl-4,5,6,7-tetrahydro-1,3-diiminoisoindoline
4,5,6,7-Tetraethyl-1,3-diiminoisoindoline
4,5,7-Trimethyl-1,3-diiminoisoindoline
4-Isopropyl-7-methyl-1,3-diiminoisoindoline
4,7-Dimethoxy-1,3-diiminoisoindoline
5,6-Dimethoxy-4,5,6,7-tetrahydro-1,3-diiminoisoindoline
4,5-Dipropyl-7-ethoxy-1,3-diiminoisoindoline
5-Ethoxy-1,3-diiminoisoindoline, mp 217°–218° C (3)
4,5,7-Trimethoxy-1,3-diiminoisoindoline
4,7-Diethoxy-1,3-diiminoisoindoline
4-Chloro-1,3-diiminoisoindoline (3)
5-Bromo-1,3-diiminoisoindoline
5-Chloro-4,5,6,7-tetrahydro-1,3-diiminoisoindoline
5,6-Dichloro-1,3-diiminoisoindoline, mp 265° C (dec) (1)
4,5,6,7-Tetrachloro-1,3-diiminoisoindoline, mp 295°–300° C (dec) (1)
5,6-Dibromo-4,7-difluoro-1,3-diiminoisoindoline
5-Chloro-4,6,7-trifluoro-1,3-diiminoisoindoline
4-Bromo-6-methyl-4,5,6,7-tetrahydro-1,3-diiminoisoindoline
5,6-Diiodo-4,7-dimethoxy-1,3-diiminoisoindoline
4,7-Difluoro-1,3-diiminoisoindoline
4,5,6,7-Tetrabromo-1,3-diiminoisoindoline
5-Phenyl-1,3-diiminoisoindoline (3)
4-Methyl-5,6,7-triphenyl-1,3-diiminoisoindoline
5-Methyl-4-phenyl-4,5,6,7-tetrahydro-1,3-diiminoisoindoline
4-(3,4-Dimethoxyphenyl)-4,5,6,7-tetrahydro-1,3-diiminoisoindoline
7-Ethoxy-4-methyl-5-phenyl-1,3-diiminoisoindoline
4-(p-Chlorophenyl)-4,5,6,7-tetrahydro-1,3-diiminoisoindoline
4-(p-Bromophenyl)-7-phenyl-4,5,6,7-tetrahydro-1,3-diiminoisoindoline
4,5,7-Triphenyl-4,5,6,7-tetrahydro-1,3-diiminoisoindoline
4,5,6,7-Tetraphenyl-1,3-diiminoisoindoline
5-(2,4,5-Trimethylphenyl)-1,3-diiminoisoindoline
5,6-Diphenyl-1,3-diiminoisoindoline (3)
5-Phenoxy-1,3-diiminoisoindoline, mp 99° C (3)
5-Methoxy-1,3-diiminoisoindoline, mp 202° C (dec) (3)
5-(2',5'-Dimethoxyphenyl)-1,3-diiminoisoindoline
5-Chloro-1,3-diiminoisoindoline
6,7-Dichloro-1,3-diiminoisoindoline
7-Chloro-1,3-diiminoisoindoline An alternate but similar route to the preparation of the novel 1-imino-3-(4-imino-5-thiazolidinylidene)isoindolines and 1-imino-3-(4-imino-2-thiazolin-5-ylidene)isoindolines represented by Formula VI comprises the condensation of the appropriate 1-imino-3-lower-alkoxyisoindoline or 1-imino-3-mercaptoisoindoline through the alkoxy or mercapto moiety respectively at the site of the active methylene moiety of the appropriate 4-iminothiazolidine or 4-imino-2-thiazoline. Although either the appropriate 1-imino-3-lower-alkoxyisoindoline or 1-imino-3-mercaptoisoindoline may be substituted in the preparative route described above which utilizes the appropriate 1,3-diiminoisoindoline, a particularly convenient procedure involves in a single operation the in situ formation of the 1-imino-3-lower-alkoxyisoindoline or 1-imino-3-mercaptoisoindoline and the condensation thereof with the appropriate iminothiazolidine or iminothiazoline. Thus, in a manner taught in the prior art an appropriate phthalonitrile is treated at ambient temperature in a lower-aliphatic alcohol, such as methanol, with one molecular equivalent of either a sodium lower-alkoxide to obtain the 1-imino-3-loweralkoxyisoindoline or with sodium sulfide to obtain the corresponding sodio derivative of 1-imino-3-mercaptoisoindoline. Then under an atmosphere of nitrogen one molecular equivalent of the appropriate iminothiazolidine or iminothiazoline in the form of the acid addition salt is added to the stirred reaction mixture at 0° C and stirring is continued for approximately 16 to 18 hours whilst permitting the reaction to warm gradually to room temperature.

The thiazolidines represented by Formula XII when Y is

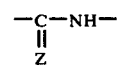

and the 2-thiazolines when Y is

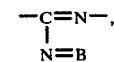

which are required for condensation with the 1,3-diiminoisoindolines to obtain the novel 1-imino-3-(4-imino-5-thiazolidinylidene)isoindolines and the 1-imino-3-(4-imino-2-thiazolin-5-ylidene)isoindolines, respectively, of Formula VI are generally known in the art and are conveniently prepared by employing known chemical procedures. For example, the known 2,4-diiminothiazolidine (Formula XII where Y is

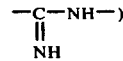

is obtained by the interaction of a haloacetonitrile with thiourea.

The starting material, 2,4-diiminothiazolidine, also serves as the starting material for the preparation of the known compound, 4-imino-2-thiazolidinone (Formula XII where Y is

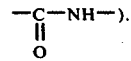

Thus, 2,4-diiminothiazolidine is in a first step hydrolyzed to obtain 2,4-dioxothiazolidine which is then in the second step interacted with phosphorus pentasulfide to obtain 2-oxo-4-thioxothiazolidine. Finally, in a third step, this intermediate is treated with ammonium hydroxide to convert the 4-thioxo moiety to an imino group thus yielding the desired 4-imino-2-thiazolidinone.

The starting material 4-imino-2-thiazolidinethione (Formula XII where Y is

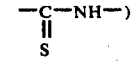

is similarly prepared by first interacting commercially available 4-oxo-2-thioxothiazolidine with phosphorus pentasulfide to produce 2,4-dithioxothiazolidine which upon treatment with ammonium hydroxide yields the desired 4-imino-2-thiazolidinethione.

The 2-amino-substituted-4-imino-2-thiazoline starting materials depicted by Formula XII wherein Y represents

are conveniently prepared by the interaction of a haloacetonitrile and the appropriately substituted thiourea of the formula

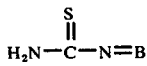

wherein N=B has VI same respective meanings given for Formulas I, III, V Vi and VIII above. For example, the following compounds of Formula XII (named as the free base) are useful starting materials for condensation with the 1,3-diiminoisoindoline starting materials described above for obtaining the novel 1-imino-3-(2-amino-substituted-4-imino-2-thiazolin-5-ylidene)isoindolines of Formula VI in which Y is N=B.

2-Methylamino-4-imino-2-thiazoline
2-Isopropylamino-4-imino-2-thiazoline
2-(2-Methylbutylamino)-4-imino-2-thiazoline
2-n-Hexylamino-4-imino-2-thiazoline
2-Anilino-4-imino-2-thiazoline
2-Diethylamino-4-imino-2-thiazoline
2-N-Methylethylamino-4-imino-2-thiazoline
2-Di-t-butylamino-4-imino-2-thiazoline
2-Di-n-hexylamino-4-imino-2-thiazoline
2-Benzylamino-4-imino-2-thiazoline
2-(3-Phenylpropylamino)-4-imino-2-thiazoline
2-(5-Phenylpentylamino)-4-imino-2-thiazoline
2-N-Ethylanilino-4-imino-2-thiazoline
2-N-Butylanilino-4-imino-2-thiazoline
2-(p-Ethylanilino)-4-imino-2-thiazoline
2-Dibenzylamino-4-imino-2-thiazoline
2-N-Ethylbenzylamino-4-imino-2-thiazoline
2-(p-Chloroanilino)-4-imino-2-thiazoline
2-(o-Methoxyanilino)-4-imino-2-thiazole
2-N-Methyl(p-bromobenzylamino)-4-imino-2-thiazole
2-Pyrrolidino-4-imino-2-thiazoline
2-Piperidino-4-imino-2-thiazoline
2-Morpholino-4-imino-2-thiazoline
2-(2-Methylpiperidino)-4-imino-2-thiazoline
2-(3-Ethylpyrrolidino)-4-imino-2-thiazoline
2-(3-Methylmorpholino)-4-imino-2-thiazoline The structures of the compounds of this invention were established by the modes of synthesis, by elementary analyses of representative samples, and by ultraviolet, infrared and nuclear magnetic resonance spectral analyses. The course of the reactions for the preparation of the intermediates and their consumption in the chelating reactions was followed by the use of thin layer chromatography.

The invention is illustrated by the following examples without, however, being limited thereto. Melting points are uncorrected unless otherwise indicated. In the following examples, the term "parts" is in each instance used to indicate parts by weight and the relationship of parts by weight to parts by volume is the same as that of the kilogram to the liter.

EXAMPLE 1

A. To a stirred solution of 61 parts of 28 percent aqueous ammonium hydroxide solution and 2500 parts of water under at atmosphere of nitrogen there was simultaneously added at ambient temperature during a period of ninety minutes 273 parts of 2,4-diiminothiazolidinium benzenesulfonate and 853 parts of a 17.1 percent by weight methyl alcohol solution of 1,3-diiminoisoindoline. A yellow solid separated during the addition. Stirring was continued at room temperature for approximately sixteen hours after the additions were complete and the thick yellow reaction slurry was then filtered. The product collected on the funnel was washed copiously with distilled water and finely dried at 50° C in vacuo to obtain 233 parts of 1-imino-3-(2,4-diimino-5-thiazolidinylidene)-isoindoline as a yellow solid melting at 252°–263° C (dec.).

Anal. Calcd. for $C_{11}H_9N_5S$: C, 54.30; H, 3.73; N, 28.79; S, 13.18. Found: C, 54.15; H, 3.85; N, 28.63; S, 12.92.

This compound, which corresponds to Formula VII wherein R, $R_1$, $R_2$ and $R_3$ are each hydrogen, and Z is NH, was found on testing in vitro by standard serial dilution procedures to be bacteriostatic versus *Salmonella typhosa* Hopkins at a concentration of 250 parts per million and bactericidal at 750 parts per million; and both bacteriostatic and bactericidal versus *Clostridium welchii* M at 100 parts per million.

B. To a stirred solution of 150 parts of zinc chloride in 2280 parts of dimethylformamide there was added at ambient temperature 243 parts of 1-imino-3-(2,4-diimino-5-thiazolidinylidene)isoindoline which went into solution. After approximately 5 to 10 minutes of continued stirring, the zinc chloride adduct began to separate from the reaction mixture as a yellow precipitate. Stirring at room temperature was continued overnight after which the product was collected by filtration, washed first with fresh dimethylformamide, then with acetone and finally dried in a vacuum oven at 50° C to obtain 390 parts of the zinc chloride adduct of 1-imino-3(2,4-diimino-5-thiazolidinylidene)isoindoline as a yellow powder which melted at 337°–338° C (dec).

Anal. Calcd. for $C_{11}H_9N_5S \cdot ZnCl_2$: C, 35.28; H, 2.44; N, 18.50; S, 8.46; Cl, 17.94; Zn, 16.68. Found: C, 34.81; H, 2.39; N, 18.45; S, 8.45; Cl, 18.68; Zn, 17.22.

When the above-described procedure was employed but zinc bromide was used in place of zinc chloride, the zinc bromide adduct of 1-imino-3-(2,4-diimino-5-thiazolidinylidene)isoindoline was obtained as a yellow powder which melted at 347°–348° C (dec).

C. To a stirred solution of 130.5 parts of nickel (II) chloride hexahydrate in 2260 parts of dimethylformamide, there was added at room temperature 380 parts of the zinc chloride adduct of 1-imino-3-(2,4-diimino-5-thiazolidinylidene)isoindoline from B. The reaction slurry was then stirred at ambient temperature for a period of 4 hours during which the mixture gradually changed from yellow to deep red. During the next 2 hours, the slurry was gradually heated to 100° C and was maintained at that temperature for 4 hours. Ammonia was evolved during the reaction period. The suspended red solid was then collected by filtration, washed successively with fresh dimethylformamide, water and finally acetone. The solid was then dried in vacuo at 50° C to obtain 285 parts of the blue-red nickel chelate pigment represented by Formula II wherein Me is Ni; Z is NH; R, $R_1$, $R_2$ and $R_3$ are each hydrogen and An is Cl.

Anal. Calcd. for $C_{22}H_{14}ClN_9NiS_2$: C, 46.96; H, 2.50; Cl, 6.31; N, 22.41; Ni, 10.43; S, 11.40. Found: C, 43.97; H, 2.81; Cl, 5.66; N, 20.21; Ni, 9.76; S, 10.65; $H_2O$ 7.45; (On dry basis) C, 47.51; H, 2.23; Cl, 6.11; N, 21.84; Ni, 10.55; S, 11.51.

EXAMPLE 2

A mixture of 4.35 parts of 1,3-diiminoisoindoline and 50 parts of dimethylformamide was stirred and heated to 50° C to effect complete solution. The solution was cooled to a temperature in the range 15° to 20° C and there was then added a solution of 3.92 parts of nickel (II) chloride hexahydrate in 30 parts of dimethylformamide. Stirring was continued for 30 minutes after the addition during which period a yellow solid gradually deposited from the solution. To the stirred suspension there was then added 8.2 parts of 2,4-diiminothiazolidinium benzenesulfonate. Stirring was continued at room temperature for approximately 16 hours. A red solid gradually separated from the reaction mixture during the stirring period. The mixture was then heated at 100° C for 5 hours after which the product was collected by filtration, washed successively with dimethylformamide, water and acetone. Ths product was dried in vacuo to obtain 7.3 parts of the nickel chelate pigment which corresponds to Formula II wherein Me is Ni; Z is NH; R, $R_1$, $R_2$ and $R_3$ are each hydrogen; and An is Cl. The product has the same blue-red shade as the product obtained in Example 1, part C, above.

EXAMPLE 3

A. A mixture of 25.5 parts of 1,3-diimino-4,5,6,7-tetrachloroisoindoline, 13.65 parts of 2,4-diiminothiazolidine hydrochloride and 600 parts of dimethylformamide was stirred and heated under an atmosphere of nitrogen at a temperature in the range 65°–70° C for approximately 16 hours. The reaction mixture was then cooled to 10° C and filtered. The collected solid was washed with 60 parts of fresh dimethylformamide, slurried with 1200 parts of a 10 percent aqueous solution of sodium carbonate and then refiltered. The collected solid was recrysallized from hot glacial acetic acid to obtain 1-imino-4,5,6,7- tetrachloro-3-(2,4-diimino-5-thiazolidinylidene)isoindoline acetate as a brown powder melting with gradual decomposition above 200° C.

Anal. Calcd. for $C_{11}Cl_4H_5N_5S \cdot C_2H_4O$: C, 35.39; H, 2.06; Cl, 32.15; N, 15.88; S, 7.27. Found: C, 35.47; H, 2.15; Cl, 32.87; N, 16.11; S, 7.43.

This compound, which corresponds to Formula VII wherein R, $R_1$, $R_2$ and $R_3$ are each Cl, and Z is NH, was found on testing in vitro by standard serial dilution procedures to be bacteriostatic versus: *Staphylococcus aureus* 209 at a minimal concentration of 31.3 parts per million; *Pseudomonas aeruginosa* 211 at 62.5 parts per million; *Esherichia coli* at 62.5 parts per million; and *Proteus vulgaris* ATCC 9920 at 125 parts per million.

B. To a stirred solution of 2.5 parts of nickel (II) chloride hexahydrate in 500 parts of hexamethylphosphoramide, there was added at room temperature during a period of 30 minutes, 7.6 parts of 1-imino-4,5,6,7-tetrachloro-3-(2,4-diimino-5-thiazolidinylidene)isoindoline obtained by treating the acetate-salt form of A above with methanolic triethylamine. After the addition was complete, the reaction mixture was stirred at room temperature for 16 hours and then filtered. The collected solid was washed with fresh hexamethylphosphoramide, then with water and finally dried in vacuo at 100° C to obtain the dark-red pigment corresponding to Formula II in which Me is Ni; Z is NH; R, $R_1$, $R_2$ and $R_3$ are each Cl; and An is Cl.

Anal. Calcd. for $C_{22}H_6Cl_9N_9NiS_2$: C, 31.52; H, 0.72; Cl, 38.06; N, 15.04; Ni, 7.01; S, 7.65. Found: C, 31.36; H, 0.73; Cl, 37.88; N, 14.97; Ni, 7.29; S, 7.74.

EXAMPLE 4

A. A mixture of 3.5 parts of 4-imino-2-thiazolidinone, 4.4 parts of 1,3-diiminoisoindoline and 100 parts of methanol was stirred under an atmosphere of nitrogen at room temperature for three hours and then at reflux temperature for 2 hours. The reaction mixture was cooled to 25° C and the solid therein was collected by filtration, washed with fresh methanol and dried in varuo at 50° C to obtain 5.4 parts of 1-imino-3-(2-oxo-4-imino-5-thiazolidinylidene)isoindoline as a yellow powder melting at 346°–348° C (dec).

Anal. Calcd. for $C_{11}H_8N_4OS$ (M.W. 244.25): N, 22.94; S, 13.13. Found: N, 23.00; S, 13.28.

Mass spectrum determination showed a parent peak at $M^+$ 244. This compound corresponds to Formula VII wherein R, $R_1$, $R_2$ and $R_3$ are each hydrogen and Z is O.

B. To a stirred solution of 2.7 parts of nickel toluenesulfonate hexahydrate in 100 parts of dimethylformamide there was added at room temperature 2.44 parts of 1-imino-3-(2-oxo-4-imino-5-thiazolidinylidene)isoindoline. The temperature of the reaction mixture was gradually raised to reflux over a period of 3 hours and maintained for an additional hour. The reaction mixture which gradually changed color from yellow to dark red during the heating period, was cooled to 25° C and the solid therein collected by filtration. After successive washings with dimethylformamide, water and finally acetone, the solid was dried in vacuo to obtain 2.2 parts of the red pigment represented by Formula II in which Me is Ni, Z is O; R, $R_1$, $R_2$ and $R_3$ are each hydrogen; and An is OH.

Anal. Calcd. for $C_{22}H_{12}N_7NiO_3S_2$: C, 48.46; H, 2.22; N, 17.98; Ni, 10.77; S, 11.77. Found: C, 48.96; H, 2.16; N, 18.01; Ni, 10.90; S, 11.64.

EXAMPLE 5

Three parts of the nickel (II) chloride chelate pigment obtained in Example 1C was dissolved in 39 parts of methanesulfonic acid at approximately 75° C under an atmosphere of nitrogen. To the stirred solution was added 19.2 parts of water after which heating was effected to and held at 125° C for 5 hours. A red solid gradually separated during the heating period. The reaction mixture was cooled to 25° C and filtered. The collected solid was washed successively with aqueous methanesulfonic acid, water and acetone and finally dried in vacuo to obtain the nickel chelate pigment represented by Formula II wherein Me is Ni; Z is O, R, $R_1$, $R_2$ and $R_3$ are each hydrogen; and An is OH. This product was of the same shade and hue as that obtained in Example 4, part B, above and had an infrared spectrum identical to that obtained for the product of Example 4, part B above.

Anal. Calcd. for $C_{22}H_{12}N_7NiO_3S_2$: C, 48.46; H, 2.22; N, 17.98; Ni, 10.77; S, 11.77. Found: C, 48.30; H, 2.33; N, 17.74; Ni, 10.55; S, 11.14.

EXAMPLE 6

To a stirred solution of 178 parts of p-toluenesulfonic acid in 22 parts of water warmed to approximately 85° C, there was added ten parts of the nickel (II) chloride chelate pigment obtained in Example 1C above. The reaction mixture was heated at reflux for a period of approximately 19 hours during which a red solid gradually separated. The solid was collected by filtration and washed successively with a 70 percent aqueous solution of p-toluenesulfonic acid, water, and finally acetone. The product was dried in vacuo to obtain 8.8 parts of the blue-red pigment corresponding to Formula II wherein Me is Ni; R, $R_1$, $R_2$ and $R_3$ are each hydrogen; Z is O, and An is p-$(CH_3)C_6H_4SO_3$.

Anal. Calcd. for $C_{29}H_{19}N_7NiO_5S_3$: C, 49.73; H, 2.73; N, 14.00; Ni, 8.38; S, 13.73. Found: C, 49.59; H, 2.82; N, 14.19; Ni, 8.15; S, 13.60.

EXAMPLE 7

To a stirred suspension of 9.7 parts of 1-imino-3-(2,4-diimino-5-thiazolidinylidene)isoindoline in 100 parts of hexamethylphosphoramide there was added 3.45 parts of copper (II) chloride dihydrate. The reaction mixture was stirred at room temperature for approximately 16 hours and was then heated to and held at 100° C for four hours. The mixture was filtered and the collected solid was washed with fresh hexamethylphosphoramide and finally with water. The product was dried in vacuo to obtain the dark red copper chelate pigment represented by Formula II wherein Me is Cu; Z is NH; R, $R_1$, $R_2$ and $R_3$ are each hydrogen; and An is Cl.

EXAMPLE 8

Following the procedure described above in Example 7, but substituting 4.8 parts of cobalt (II) chloride hexahydrate for the copper (II) chloride dihydrate used in that example, there was obtained the brown cobalt chelate pigment corresponding to Formula II wherein Me is Co; Z is NH; R, $R_1$, $R_2$ and $R_3$ are each hydrogen; and An is Cl.

EXAMPLE 9

A. A mixture of 33.1 parts of 1-piperidyl thiocarbamide, 140 parts of ethyl alcohol and 17.4 parts of chloroacetonitrile was heated at reflux for 1½ hours. The reaction mixture was then chilled in an ice bath to less than 10° C and filtered. The white crystalline solid isolated by the filtration was dried to obtain 26 parts of 2-piperidino-4-imino-2-thiazoline hydrochloride which gradually softened above 200° C and decomposed at 321° C. An additional 21 parts of the product were obtained by concentrating the filtrate.

Anal. Calcd. for $C_8H_{13}N_3S$ . HCl: C, 43.73; H, 6.42; Cl, 16.13; N, 19.12; S, 14.59. Found: C, 43.77; H, 6.36; Cl, 16.14; N, 19.25; S, 14.56.

B. To a solution of 21.9 parts of 2-piperidino-4-imino-2-thiazoline hydrochloride in 240 parts of methyl alcohol there was added 14.5 parts of 1,3-diiminoisoindoline. The resultant mixture was heated at reflux for six hours, then chilled to 0° C and filtered. The collected solid was washed with methyl alcohol and dried at 50° C to obtain 27 parts of 1-imino-3-(2-piperidino-4-imino-2-thiazolin-5-ylidene)isoindoline hydrochloride melting at 320°–321° C (dec). The assigned chemical structure was completely corroborated by a concordant nuclear magnetic resonance spectrum.

The hydrochloride salt is readily converted to the free base, a colorless solid melting at 226°–227°C, by treatment with dilute ammonium hydroxide. This compound, which corresponds to Formula VIII wherein R, $R_1$, $R_2$ and $R_3$ are each hydrogen and N=B is piperidino, was found on testing in vitro by standard serial dilution procedures to be bacteriostatic versus: *Staphylococcus aureus* 209 at a minimal concentration of 6.3 parts per million; *Esherichia coli* at 62.5 parts per million; *Pseudomonas aeruginosa* 211 at 125 parts per million; and fungicidal versus *Tricophyton mentogrophytes* at 62.5 parts per million; *Aspergillus niger* at > 125 parts per million; and Candida albicans at 125 parts per million.

C. To a solution of 0.5 part of nickel (II) chloride hexahydrate in 40 parts of methyl alcohol there was added at 25° C 1.2 parts of 1-imino-3-(2-piperidino-4-imino-2-thiazolin-5-ylidene)isoindoline. A deep red solution resulted which was stirred at 25° C for 2 hours and was then heated at reflux for 2 hours. To the solution there was added 80 parts of dioxane. The solid, which separated from the solution, was collected by filtration, washed with 75 percent aqueous dioxane solution and finally dried in vacuo at 100° C to obtain 1.1 parts of dark red pigment which remained unmelted at 345° C. This product, which corresponds to Formula III wherein Me is Ni; R, $R_1$, $R_2$ and $R_3$ are each hydrogen; N=B is piperidino; and An is Cl, was found to be solvated by one mole of water and one mole of methyl alcohol.

Anal. Calc'd for $C_{32}H_{30}ClN_9NiS_2$ . $CH_3OH$ . $H_2O$: C, 52.91; H, 4.84; Cl, 4.74; N, 16.83; Ni, 7.84; S, 8.56. Found: C, 52.36; H, 4.20; Cl, 4.42; N, 16.07; Ni, 7.73; S, 8.35. Nuclear magnetic resonance spectrum was concordant for the solvated assigned structure.

EXAMPLE 10

A. A mixture of 6 parts of 2,4-diiminothiazolidine hydrochloride, 6 parts of 4,5,6,7-tetrahydro-1,3-diiminoisoindoline and 100 parts of anhydrous methyl alcohol was stirred and heated at reflux under an atmosphere of nitrogen for approximately 16 hours. The reaction was then cooled and filtered. The solid product collected by filtration was converted to the free base by treatment with a slight excess of a methyl alcohol solution of triethylamine and the product thus obtained was recrystallized from acetic acid. The resultant acetate salt was treated with dilute ammonium hydroxide and the product isolated to obtain in the free-base form 1-imino-4,5,6,7-tetrahydro-3(2,4-diimino-5-thiazolidinylidene)isoindoline as a greenish-brown powder melting at 215°–223° C (dec).

Anal. Calc'd for $C_{11}H_{13}N_5S$: C, 53.42; H, 5.30; N, 28.32; S, 12.96. Found: C, 53.37; H, 5.29; N, 28.20; S, 13.10.

This compound, which corresponds to Formula IX wherein R, $R_1$, $R_2$ and $R_3$ are each hydrogen and Z is NH, was found on testing in vitro by standard serial dilution procedures to be bacteriostatic versus: *Staphylococcus aureus* 209 at a minimal concentration of 31.3 parts per million; *Pseudomonas aeruginosa* 211 at 125 parts per million; *Esherichia coli* at 125 parts per million; and *Proteus vulgaris* ATCC 9920 at 125 parts per million.

B. Following a procedure similar to that described in Example 3, part B hereinabove, 7.3 parts of the 1-imino-4,5,6,7-tetrahydro-3-(2,4-diimino-5-thiazolidinylidene)isoindoline obtained in A, was interacted with 3.75 parts of nickel (II) chloride hexahydrate in 350 parts of hexamethylphosphoramide to obtain the dark blue-red pigment corresponding to Formula IV wherein Me is Ni; R, $R_1$, $R_2$ and $R_3$ are each hydrogen; Z is NH; and An is Cl.

Anal. Calc'd for $C_{22}H_{22}ClN_9NiS_2$: C, 46.31; H, 3.89; Cl, 6.21; N, 22.08; Ni, 10.29; S, 11.24. Found: C, 46.50; H, 3.82; Cl, 6.08; N, 22.10; Ni, 10.48; S, 11.30.

EXAMPLE 11

A. When an equivalent amount of 4-imino-2-thiazolidinethione is substituted for the 4-imino-2-thiazolidinone used in the procedure described in Example 4, part A above, there is obtained as the product 1-imino-3-(2-thioxo-4-imino-5-thiazolidinylidene)isoindoline.

B. Following the procedure described in Example 4, part B above but using an equivalent amount of 1-imino-3-(2-thioxo-4-imino-5-thiazolidinylidene)isoindoline in place of 1-imino-3-(2-oxo-4-imino-5-thiazolidinylidene)isoindoline, there is obtained as the product a metal chelate pigment corresponding to Formula II in which Me is Ni; Z is S; R, $R_1$, $R_2$ and $R_3$ are each hydrogen; and An is OH.

EXAMPLE 12

A. When equivalent amounts of 2-methylamino-4-imino-2-thiazoline hydrochloride and 5,6-dichloro-1,3-diiminoisoindoline are substituted for the 2,4-diiminothiazolidine hydrochloride and 1,3-diimino-4,5,6,7-tetrachloroisoindoline respectively in the procedure described in Example 3, part A above, there is obtained as the product 1-imino-5,6-dichloro-3-(2-methylamino-4-imino-2-thiazolin-5-ylidene)isoindoline acetate.

B. Following the procedure described in Example 3, part B above but using an equivalent amount of 1-imino-5,6-dichloro-3-(2-methylamino-4-imino-2-thiazolin-5-ylidene)isoindoline acetate in place of 1-imino-4,5,6,7-tetrachloro-3-(2,4-diimino-5-thiazolidinylidene)isoindoline acetate, there is obtained as the product a metal chelate pigment corresponding to Formula III in which Me is Ni; N=B is $HNCH_3$; R and $R_3$ are each hydrogen; $R_1$ and $R_2$ are each Cl; and An is Cl.

EXAMPLE 13

A. When an equivalent amount of 4,5-dipropyl-7-ethoxy-1,3-diiminoisoindoline is substituted for the 1,3-diiminoisoindoline used in the procedure described in Example 1, part A above, there is obtained as the product 1-imino-4,5-dipropyl-7-ethoxy-3-(2,4-diimino-5-thiazolidinylidene)isoindoline.

B. Following the procedure described in Example 7 above but using an equivalent amount of 1-imino-4,5-dipropyl-7-ethoxy-3-(2,4-diimino-5-thiazolidinylidene)isoindoline in place of 1-imino-3-(2,4-diimino-5-thiazolidinylidene)isoindoline, there is obtained as the product a metal chelate pigment corresponding to Formula II in which Me is Cu; Z is NH; R is $OC_2H_5$, $R_2$ and $R_3$ are each $C_3H_7$; $R_1$ is hydrogen; and An is Cl.

EXAMPLE 14

A. When equivalent amounts of 5-methyl-1,3-diiminoisoindoline and 4-imino-2-thiazolidinethione are substituted for the 1,3-diiminoisoindoline and 4-imino-2-thiazolidinone respectively, in the procedure described in Example 4, part A above, there is obtained as the product 1-imino-5-methyl-3-(2-thioxo-4-imino-5-thiazolidinylidene)isoindoline.

B. Following the procedure described in Example 4, part B above but using an equivalent amount of 1-imino-5-methyl-3-(2-thioxo-4-imino-5-thiazolidinylidene)isoindoline in place of 1-imino-3-(2-oxo-4-imino-5-thiazolidinylidene)isoindoline, there is obtained as the product a metal chelate pigment corresponding to Formula II in which Me is Ni; Z is S; $R_2$ is $CH_3$; R, $R_1$ and $R_3$ are each hydrogen; and An is OH.

EXAMPLE 15

A. When equivalent amounts of 4,5,6,7-tetraethyl-1,3-diiminoisoindoline and 2-isopropylamino-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-4,5,6,7-tetraethyl-3-(2-isopropylamino-4-imino-2-thiazolin-5-ylidene)isoindoline hydrochloride.

B. Following the procedure described in Example 9, part C above but using an equivalent amount of 1-imino-4,5,6,7-tetraethyl-3-(2-isopropylamino-4-imino-2-thiazolidin-5-ylidene)isoindoline in the free-base form in place of 1-imino-3-(2-piperidino-4-imino-2-thiazolin-5-ylidene)isoindoline, there is obtained as the product a metal chelate pigment corresponding to Formula III in which Me is Ni; R, $R_1$, $R_2$ and $R_3$ are each $C_2H_5$; N=B is iso-$C_3H_7NH$; and An is Cl.

EXAMPLE 16

A. When equivalent amounts of 4,7-dimethoxy-1,3-diiminoisoindoline and 2-(2-methylbutylamino)-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-4,7-dimethoxy-3-[2-(2-methylbutylamino)-4-imino-2-thiazolin-5-ylidene]isoindoline hydrochloride.

B. Following the procedure described in Example 9, part C above but using an equivalent amount of 1-imino-4,7-dimethoxy-1-[2-(2-methylbutylamino)-4-imino-2-thiazolin-5-ylidene]isoindoline in the free-base form in place of 1-imino-3-(2-piperidino-4-imino-2-thiazolin-5-ylidene)isoindoline, there is obtained as the product a metal chelate pigment corresponding to Formula III in which Me is Ni; R and $R_3$ are each $OCH_3$; $R_1$ and $R_2$ are each hydrogen; N=B is $NHCH_2CH(CH_3)CH_2CH_3$; and An is Cl.

EXAMPLE 17

A. When equivalent amounts of 4-chloro-1,3-diiminoisoindoline and 2-n-hexylamino-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-4-chloro-3-(2-n-hexylamino-4-imino-2-thiazolin-5-ylidene)isoindoline hydrochloride.

B. Following the procedure described in Example 8 above but using an equivalent amount of 1-imino-4-chloro-3-(2-n-hexylamino-4-imino-2-thiazolin-5-ylidene)isoindoline in the free-base form in place of 1-imino-3-(2,4-diimino-5-thiazolidinylidene)isoindoline, there is obtained as the product a metal chelate pigment corresponding to Formula III in which Me is Co; $R_3$ is Cl; R, $R_1$ and $R_2$ are each hydrogen; N=B is NH-n-$C_6H_{13}$; and An is Cl.

EXAMPLE 18

A. When equivalent amounts of 4,5-dimethyl-1,3-diiminoisoindoline and 2-anilino-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-4,5-dimethyl-3-(2-anilino-4-imino-2-thiazolin-5-ylidene)isoindoline hydrochloride.

B. Following the procedure described in Example 9, part C above but using equivalent amounts of 1-imino-4,5-dimethyl-3-(2-anilino-4-imino-2-thiazolin-5-ylidene)isoindoline in the free-base form and nickel (II) bromide trihydrate in place of 1-imino-3-(2-piperidino-4-imino-2-thiazolin-5-ylidene)isoindoline and nickel (II) chloride hexahydrate respectively, there is obtained as the product a metal chelate pigment corresponding to Formula III in which Me is Ni; $R_2$ and $R_3$ are each $CH_3$; R and $R_1$ are each hydrogen; N=B is $NHC_6H_5$; and An is Br.

EXAMPLE 19

A. When an equivalent amount of 5-bromo-1,3-diiminoisoindoline is substituted for the 1,3-diiminoisoindoline in the procedure described in Example 4, part A above, there is obtained as the product 1-imino-5-bromo-3-(2-oxo-4-imino-5-thiazolidinylidene)isoindoline.

B. Following the procedure described in Example 4, part B above but using an equivalent amount of 1-imino-5-bromo-3-(2-oxo-4-imino-5-thiazolidinylidene)isoindoline in place of 1-imino-3-(2-oxo-4-imino-5-thiazolidinylidene)isoindoline, there is obtained as the product a metal chelate pigment corresponding to Formula II in which Me is Ni; $R_2$ is Br; R, $R_1$ and $R_3$ are each hydrogen; Z is O; and An is OH.

EXAMPLE 20

A. Following the procedure described in Example 9, part B above but using equivalent amounts of 5,6-diiodo-4,7-dimethoxy-1,3-diiminoisoindoline and 2-diethylamino-4-imino-2-thiazoline hydrochloride in place of 1,3-diiminoisoindoline and 2-piperidino-4-imino-2-thiazoline hydrochloride respectively, there is obtained as the product 1-imino-5,6-diiodo-4,7-dimethoxy-3-(2-diethylamino-4-imino-2-thiazolin-5-ylidene)isoindoline hydrochloride.

B. When an equivalent amount of 1-imino-5,6-diiodo-4,7-dimethoxy-3-(2-diethylamino-4-imino-2-thiazolin-5-ylidene)isoindoline in the form of the free base is substituted for the 1-imino-3-(2-piperidino-4-imino-2-thiazolin-5-ylidene)isoindoline in the procedure described in Example 9, part C above, there is obtained as the product a metal chelate pigment corresponding to Formula III in which Me is Ni; R and $R_3$ are each $OCH_3$; $R_1$ and $R_2$ are each I; N=B is $N(C_2H_5)_2$; and An is Cl.

EXAMPLE 21

A. When the procedure described in Example 9, part B above is followed but using equivalent amounts of 4,5,6,7-tetrabromo-1,3-diiminoisoindoline and 2-N-methylethylamino-4-imino-2-thiazoline hydrochloride in place of the 1,3-diiminoisoindoline and 2-piperidino-4-imino-2-thiazoline hydrochloride respectively, there is obtained as the product 1-imino-4,5,6,7-tetrabromo-3-(2-N-methylethylamino-4-imino-2-thiazolin-5-ylidene)isoindoline hydrochloride.

B. Following the procedure described in Example 7 above but using an equivalent amount of 1-imino-4,5,6,7-tetrabromo-3-(2-N-methylethylamino-4-imino-2-thiazolin-5-ylidene)isoindoline in the free-base form in place of 1-imino-3-(2,4-diimino-5-thiazolidinylidene)isoindoline, there is obtained as the product a metal chelate pigment corresponding to Formula III in which Me is Cu; R, $R_1$, $R_2$ and $R_3$ are each Br; N=B is $N(CH_3)C_2H_5$; and An is Cl.

EXAMPLE 22

A. When equivalent amounts of 5-chloro-4,5,6,7-tetrahydro-1,3-diiminoisoindoline and 2-di-t-butylamino-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-5-chloro-4,5,6,7-tetrahydro-3-(2-di-t-butylamino-4-imino-2-thiazolin-5-ylidene)isoindoline hydrochloride.

B. Following the procedure described above in Example 8 but substituting an equivalent amount of 1-imino-5-chloro-4,5,6,7-tetrahydro-3-(2-di-t-butylamino-4-imino-2-thiazolin-5-ylidene)isoindoline in the free-base form or the 1-imino-3-(2,4-diimino-5-thiazolidinylidene)isoindoline used in that example, there is obtained the metal chelate pigment which corresponds to Formula V in which Me is Co; $R_2$ is Cl; R, $R_1$ and $R_3$ are each hydrogen; N=B is $N(t-C_4H_9)_2$; and An is Cl.

EXAMPLE 23

A. When equivalent amounts of 5-phenyl-1,3-diiminoisoindoline and 2-di-n-hexylamino-4-imino-2-thiazoline hydrochloride are substituted for the 1,3-diiminoisoindoline and 2-piperidino-4-imino-2-thiazoline hydrochloride respectively, in the procedure described in Example 9, part B above, there is obtained as the product 1-imino-5-phenyl-3-(2-di-n-hexylamino-4-imino-2-thiazolin-5-ylidene)isoindoline hydrochloride.

B. Following the procedure described in Example 9, part C above but using an equivalent amount of 1-imino-5-phenyl-3-(2-di-n-hexylamino-4-imino-2-thiazolin-5-ylidene)isoindoline in the form of the free base in place of 1-imino-3-(2-piperidino-4-imino-2-thiazolin-5-ylidene)isoindoline, there is obtained as the product a metal chelate pigment corresponding to Formula III in which Me is Ni; $R_2$ is $C_6H_5$; R, $R_1$ and $R_3$ are each hydrogen; N=B is $N(n-C_6H_{13})_2$; and An is Cl.

EXAMPLE 24

A. Proceeding in a manner similar to that described above in Example 3, part A but substituting an equivalent amount of 4,7-difluoro-1,3-diiminoisoindoline for the 1,3-diimino-4,5,6,7-tetrachloroisoindoline used in that example, there is obtained 1-imino-4,7-difluoro-3-(2,4-diimino-5-thiazolidinylidene)isoindoline acetate.

B. When an equivalent amount of 1-imino-4,7-difluoro-3-(2,4-diimino-5-thiazolidinylidene)isoindoline acetate is substituted for the 1-imino-4,5,6,7-tetrachloro-3-(2,4-diimino-5-thiazolidinylidene)isoindoline acetate in the procedure described in Example 3, part B above, there is obtained as the product a metal chelate pigment corresponding to Formula II in which Me is Ni; Z is NH; R and $R_3$ are each F; $R_1$ and $R_2$ are each hydrogen; and An is Cl.

EXAMPLE 25

A. Using a procedure similar to that described in Example 9, part B above but substituting 4-methyl-5,6,7-triphenyl-1,3-diiminoisoindoline and 2-benzylamino-4-imino-2-thiazoline hydrochloride for the 1,3-diiminoisoindoline and 2-piperidino-4-imino-2-thiazoline hydrochloride respectively, there is obtained as the product 1-imino-4-methyl-5,6,7-triphenyl-3-(2-benzylamino-4-imino-2-thiazolin-5-ylidene)isoindoline hydrochloride.

B. Following the procedure described in Example 9, part C above but using an equivalent amount of 1-imino-4-methyl-5,6,7-triphenyl-3-(2-benzylamino-4-imino-2-thiazolin-5-ylidene)isoindoline in the free-base form in place of 1-imino-3-(2-piperidino-4-imino-2-thiazolin-5-ylidene)isoindoline, there is obtained as the product a metal chelate pigment corresponding to Formula III in which Me is Ni; R, $R_1$ and $R_2$ are each $C_6H_5$; $R_3$ is $CH_3$; N=B is NH—$CH_2$—$C_6H_5$; and An is Cl.

EXAMPLE 26

A. When equivalent amounts of 5,6-dimethoxy-4,5,6,7-tetrahydro-1,3-diiminoisoindoline and 2-(3-phenylpropylamino)-4-imino-2-thiazoline hydrochloride are substituted for the 4,5,6,7-tetrahydro-1,3-diiminoisoindoline and 2,4-diiminothiazolidine hydrochloride respectively, in the procedure described in Example 10, part A above, there is obtained as the product 1-imino-5,6-di-methoxy-4,5,6,7-tetrahydro-3-[2-(3-phenylpropylamino)-4-imino-2-thiazolin-5-ylidene]isoindoline.

B. By substituting an equivalent amount of 1-imino-5,6-dimethoxy-4,5,6,7-tetrahydro-3-[2-(3-phenylpropylamino)-4-imino-2-thiazolin-5-ylidene]isoindoline for the 1-imino-3-(2,4-diimino-5-thiazolidinylidene)isoindoline in the procedure described in Example 7 above, there is obtained the metal chelate pigment represented by Formula V above wherein Me is Cu; $R_1$ and $R_2$ are each $OCH_3$; R and $R_3$ are each hydrogen; N=B is NH—$(CH_2)_3$—$C_6H_5$; and An is Cl.

EXAMPLE 27

A. Following the procedure described in Example 9, part B above but using equivalent amounts of 5,6-dichloro-1,3-diiminoisoindoline and 2-(5-phenylpentylamino)-4-imino-2-thiazoline hydrochloride in place of the 1,3-diiminoisoindoline and 2-piperidino-4-imino-2-thiazoline hydrochloride respectively, there is obtained as the product 1-imino-5,6-dichloro-3-[2-(5-phenylpentylamino)-4-imino-2-thiazolin-5-ylidene]isoindoline hydrochloride.

B. When an equivalent amount of 1-imino-5,6-dichloro-3-[2-(5-phenylpentylamino)-4-imino-2-thiazolin-5-ylidene]isoindoline in the form of the free base is substituted for the 1-imino-3-(2-piperidino-4-imino-2-thiazolin-5-ylidene)isoindoline in the procedure described in Example 9, part C above, there is obtained as the product a metal chelate pigment corresponding to Formula III in which Me is Ni; $R_1$ and $R_2$ are each Cl; R and $R_3$ are each hydrogen; N=B is NH—$(CH_2)_5$—$C_6H_5$; and An is Cl.

EXAMPLE 28

A. Following a procedure similar to that described in Example 4, part A above but substituting equivalent amounts of 5,6-dimethyl-4,5,6,7-tetrahydro-1,3-diiminoisoindoline and 4-imino-2-thiazolidenethione for the 1,3-diiminoisoindoline and 4-imino-2-thiazolidinone respectively, there is obtained as the product 1-imino-5,6-dimethyl-4,5,6,7-tetrahydro-3-(2-thioxo-4-imino-5-thiazolidinylidene)isoindoline.

When an equivalent amount of 1-imino-5,6-dimethyl-4,5,6,7-tetrahydro-3-(2-thioxo-4-imino-5-thiazolidinylidene)isoindoline is substituted for the 1-imino-3-(2,4-diimino-5-thiazolidinylidene)isoindoline in the procedure described in Example 7 above, there is obtained as the product a metal chelate pigment corresponding to Formula IV in which Me is Cu; $R_1$ and $R_2$ are each $CH_3$; R and $R_3$ are each hydrogen; Z is S; and An is Cl.

EXAMPLE 29

A. Following the procedure described in Example 9, part B above but using equivalent amounts of 4,7-diethoxy-1,3-diiminoisoindoline and 2-N-ethylanilino-4-imino-2-thiazoline hydrochloride in place of 1,3-diiminoisoindoline and 2-piperidino-4-imino-2-thiazoline hydrochloride respectively, there is obtained as the product 1-imino-4,7-diethoxy-3-(2-N-ethylanilino-4-imino-2-thiazolin-5-ylidene)isoindoline hydrochloride.

When an equivalent amount of 1-imino-4,7-diethoxy-3-(2-N-ethylanilino-4-imino-2-thiazolin-5-ylidene)isoindoline in the form of the free base is substituted for 1-imino-3-(2,4-diimino-5-thiazolidinylidene)isoindoline in the procedure described in Example 7 above, the product obtained is a metal chelate pigment corresponding to Formula III in which Me is Cu; R and $R_3$ are each $OC_2H_5$; $R_1$ and $R_2$ are each hydrogen; N=B is $N(C_2H_5)C_6H_5$; and An is Cl.

EXAMPLE 30

A. Employing a procedure similar to that described in Example 10, part A above, but substituting equivalent amounts of 5-methyl-4-phenyl-4,5,6,7-tetrahydro-1,3-diiminoisoindoline and 2-N-butylanilino-4-imino-2-thiazoline hydrochloride for 4,5,6,7-tetrahydro-1,3-diiminoisoindoline and 2,4-diiminothiazolidine hydrochloride respectively, there is obtained as the product 1-imino-5-methyl-4-phenyl-4,5,6,7-tetrahydro-3-(2-N-butylanilino-4-imino-2-thiazolin-5-ylidene)isoindoline hydrochloride.

B. When an equivalent amount of 1-imino-5-methyl-4-phenyl-4,5,6,7-tetrahydro-3-(2-N-butylanilino-4-imino-2-thiazolin-5-ylidene)isoindoline in the free-base form is substituted for the 1-imino-4,5,6,7-tetrahydro-3-(2,4-diimino-5-thiazolidinylidene)-isoindoline in the procedure described in Example 10, part B above, there is obtained as the product a metal chelate pigment corresponding to Formula V in which Me is Ni; R and $R_1$ are each hydrogen; $R_2$ is methyl; $R_3$ is phenyl; N=B is $N(C_4H_9)C_6H_5$; and An is Cl.

EXAMPLE 31

A. Proceeding in a manner similar to that described above in Example 10, part A but substituting equivalent amounts of 4-(p-chlorophenyl)-4,5,6,7-tetrahydro-1,3-diiminoisoindoline and 2-(p-ethylanilino)-4-imino-2-thiazoline hydrochloride for 4,5,6,7-tetrahydro-1,3-diiminoisoindoline and 2,4-diiminothiazolidine hydrochloride, there is obtained as the product 1-imino-4-(p-chlorophenyl)-4,5,6,7-tetrahydro-3-[2-(p-ethylanilino)-4-imino-2-thiazolin-5-ylidene]isoindoline.

B. Following the procedure described in Example 10, part B above but using an equivalent amount of 1-imino-4-(p-chlorophenyl)-4,5,6,7-tetrahydro-3-[2-(p-ethylanilino)-4-imino-2-thiazolin-5-ylidene]isoindoline in place of the 1-imino-4,5,6,7-tetrahydro-3-(2,4-diimino-5-thiazolidinylidene)isoindoline, there is obtained as the product a metal chelate pigment corresponding to Formula V in which Me is Ni; $R_3$ is p-(Cl)$C_6H_4$; R, $R_1$ and $R_2$ are each hydrogen; N=B is NH—p—($C_2H_5$)$C_6H_4$; and An is Cl.

EXAMPLE 32

A. When equivalent amounts of 5-(2,4,5-trimethylphenyl)-1,3-diiminoisoindoline and 2-dibenzylamino-4-imino-2-thiazoline hydrochloride are substituted for the 1,3-diiminoisoindoline and 2-piperidino-4-imino-2-thiazoline hydrochloride in the procedure described in Example 9, part B above, there is obtained as the product 1-imino-5-(2,4,5-trimethylphenyl)-3-(2-dibenzylamino-4-imino-2-thiazolin-5-ylidene)isoindoline hydrochloride.

B. Following the procedure described in Example 9, part C above, but using an equivalent amount of 1-imino-5-(2,4,5-trimethylphenyl)-3-(2-dibenzylamino-4-imino-2-thiazolin-5-ylidene)-isoindoline in the free-base form in place of 1-imino-3-(2-piperidino-4-imino-2-thiazolin-5-ylidene)isoindoline, there is obtained as the product a metal chelate pigment corresponding to Formula III in which Me is Ni; $R_2$ is 2,4,5—($CH_3$-)$_3$—$C_6H_2$; R, $R_1$ and $R_3$ are each hydrogen; N=B is N—($CH_2C_6H_5$)$_2$; and An is Cl.

EXAMPLE 33

A. Proceeding in a manner similar to that described above in Example 4, part A, but substituting an equivalent amount of 5-ethoxy-1,3-diiminoisoindoline for 1,3-diiminoisoindoline, there is obtained as the product 1-imino-5-ethoxy-3-(2-oxo-4-imino-5-thiazolidinylidene)isoindoline.

B. When an equivalent amount of 1-imino-5-ethoxy-3-(2-oxo-4-imino-5-thiazolidinylidene)isoindoline is substituted for 1-imino-3-(2,4-diimino-5-thiazolidinylidene)isoindoline in the procedure described in Example 8 above, there is obtained as the product a metal chelate pigment corresponding to Formula II in which Me is Co; $R_2$ is $OC_2H_5$; R, $R_1$ and $R_3$ are each hydrogen; Z is O; and An is Cl.

EXAMPLE 34

A. Following the procedure described in Example 9, part B above, but using equivalent amounts of 7-ethoxy-4-methyl-5-phenyl-1,3-diiminoisoindoline and 2-N-ethylbenzylamino-4-imino-2-thiazoline hydrochloride in place of 1,3-diiminoisoindoline and 2-piperidino-4-imino-2-thiazoline hydrochloride respectively, there is obtained as the product 1-imino-7-ethoxy-4-methyl-5-phenyl-3-(2-N-ethylbenzylamino-4-imino-2-thiazolin-5-ylidene)isoindoline hydrochloride.

B. When equivalent amounts of 1-imino-7-ethoxy-4-methyl-5-phenyl-3-(2-N-ethylbenzylamino-4-imino-2-thiazolin-5-ylidene)isoindoline in the form of the free base and nickel (II) bromide trihydrate are substituted for the 1-imino-3-(2-piperidino-4-imino-2-thiazolin-5-ylidine)isoindoline and nickel (II) chloride hexahydrate respectively, in the procedure described in Example 9, part C above, there is obtained as the product a metal chelate pigment corresponding to Formula III in which Me is Ni; R is $OC_2H_5$; $R_1$ is hydrogen; $R_2$ is $C_6H_5$; $R_3$ is $CH_3$; N=B is N($C_2H_5$)—$CH_2$—$C_6H_5$; and An is Br.

EXAMPLE 35

A. Employing a procedure similar to that described in Example 9, part B above, but substituting equivalent amounts of 4,5,7-trimethyl-1,3-diiminoisoindoline and 2-(p-chloroanilino)-4-imino-2-thiazoline hydrochloride for 1,3-diiminoisoindoline and 2-piperidino-4-imino-2-thiazoline hydrochloride respectively, there is obtained as the product 1-imino-4,5,7-trimethyl-3-[2-(p-chloroanilino)-4-imino-2-thiazolin-5-ylidene]isoindoline hydrochloride.

B. Following the procedure described in Example 9, part C above but using an equivalent amount of 1-imino-4,5,7-trimethyl-3-[2-(p-chloroanilino)-4-imino-2-thiazolin-5-ylidene]isoindoline in the free-base form in place of 1-imino-3-(2-piperidino-4-imino-2-thiazolin-5-ylidene)isoindoline, there is obtained as the product a metal chelate pigment corresponding to Formula III in which Me is Ni; R, $R_2$ and $R_3$ are each $CH_3$; $R_1$ is hydrogen; N=B is NH—p—$ClC_6H_4$; and An is Cl.

EXAMPLE 36

A. When equivalent amounts of 4-(3,4-dimethoxyphenyl)-4,5,6,7-tetrahydro-1,3-diiminoisoindoline and 2-(o-methoxyanilino)-4-imino-2-thiazoline hydrochloride are substituted for the 4,5,6,7-tetrahydro-1,3-diiminoisoindoline and 2,4-diiminothiazolidine hydrochloride respectively, in the procedure described in Example 10, part A above, there is obtained as the product 1-imino-4-(3,4-dimethoxyphenyl)-4,5,6,7-tetrahydro-3-[2-(o-methoxyanilino)-4-imino-2-thiazolin-5-ylidene]isoindoline hydrochloride.

B. Following the procedure described in Example 10, part B above, but using an equivalent amount of 1-imino-4-(3,4-dimethoxyphenyl)-4,5,6,7-tetrahydro-3-[2-(o-methoxyanilino)-4-imino-2-thiazolin-5-ylidene]isoindoline hydrochloride in place of 1-imino-4,5,6,7-tetrahydro-3-(2,4-diimino-5-thiazolidinylidene)isoindoline, there is obtained as the product a metal chelate pigment corresponding to Formula V in which Me is Ni; $R_3$ is 3,4—($OCH_3$)$_2$—$C_6H_3$; R, $R_1$ and $R_2$ are each hydrogen; N=B is NH—o—($OCH_3$)$C_6H_4$; and An is Cl.

EXAMPLE 37

A. Following the procedure described in Example 10, part A above, but using equivalent amounts of 4,5,7-triphenyl-4,5,6,7-tetrahydro-1,3-diiminoisoindoline and 2-N-methyl(p-bromobenzylamino)-4-imino-2-thiazoline hydrochloride in place of 4,5,6,7-tetrahydro-1,3-diiminoisoindoline and 2,4-diiminothiazolidine hydrochloride respectively, there is obtained as the product 1-imino-4,5,7-triphenyl-4,5,6,7-tetrahydro-3-[2-N-methyl(p-bromobenzylamino)-4-imino-2-thiazolin-5-ylidene]isoindoline.

B. When an equivalent amount of 1-imino-4,5,7-triphenyl-4,5,6,7-tetrahydro-3-[2-N-methyl(p-bromobenzylamino)-4-imino-2-thiazolin-5-ylidene]isoindoline is substituted for the 1-imino-3-(2-oxo-4-imino-5-thiazolidinylidene)isoindoline in the procedure described above in Example 4, part B, there is obtained as the product a metal chelate pigment corresponding to Formula V in which Me is Ni; R, $R_2$ and $R_3$ are each $C_6H_5$; $R_1$ is hydrogen; N=B is N(CH$_3$)—p—BrC$_6$H$_4$CH$_2$; and An is OH.

EXAMPLE 38

A. Proceeding in a manner similar to that described above in Example 3, part A, but substituting an equivalent amount of 5,6-dibromo-4,7-difluoro-1,3-diiminoisoindoline for 1-3,diimino-4,5,6,7-tetrachloroisoindoline, there is obtained as the product 1-imino-5,6-dibromo-4,7-difluoro-3-(2,4-diimino-5-thiazolidinylidene)isoindoline acetate.

B. Following the procedure described in Example 3, part B above, but using an equivalent amount of 1-imino-5,6-dibromo-4,7-difluoro-3-(2,4-diimino-5-thiazolidinylidene)isoindoline in the free-base form in place of 1-imino-4,5,6,7-tetrachloro-3-(2,4-diimino-5-thiazolidinylidene)isoindoline, there is obtained as the product a metal chelate pigment corresponding to Formula II in which Me is Ni; R and $R_3$ are each F; $R_1$ and $R_2$ are each Br; Z is NH; and An is Cl.

EXAMPLE 39

A. When equivalent amounts of 4-(p-bromophenyl)-7-phenyl-4,5,6,7-tetrahydro-1,3-diiminoisoindoline and 2-pyrrolidino-4-imino-2-thiazoline hydrochloride are substituted for the 4,5,6,7-tetrahydro-1,3-diiminoisoindoline and 2,4-diiminothiazolidine hydrochloride respectively, in the procedure described in Example 10, part A above, there is obtained as the product 1-imino-4-(p-bromophenyl)-7-phenyl-4,5,6,7-tetrahydro-3-(2-pyrrolidino-4-imino-2-thiazolin-5-ylidene)isoindoline.

B. Following the procedure described in Example 10, part B above but using an equivalent amount of 1-imino-4-(p-bromophenyl)-7-phenyl-4,5,6,7-tetrahydro-3-(2-pyrrolidino-4-imino-2-thiazolin-5-ylidene)isoindoline in place of 1-imino-4,5,6,7-tetrahydro-3-(2,4-diimino-5-thiazolidinylidene)isoindoline, there is obtained as the product a metal chelate pigment corresponding to Formula V in which Me is Ni; R is $C_6H_5$; $R_3$ is p-BrC$_6H_4$; $R_1$ and $R_2$ are each hydrogen; N=B is pyrrolidino; and An is Cl.

EXAMPLE 40

A. When an equivalent amount of 4-isopropyl-7-methyl-1,3-diiminoisoindoline is substituted for 1,3-diiminoisoindoline in the procedure described in Example 9, part B above, there is obtained as the product 1-imino-4-isopropyl-7-methyl-3-(2-piperidino-4-imino-2-thiazolin-5-ylidene)isoindoline hydrochloride.

B. Following the procedure described in Example 9, part C above, but using an equivalent amount of 1-imino-4-isopropyl-7-methyl-3-(2-piperidino-4-imino-2-thiazolin-5-ylidene)isoindoline in the form of its free base in place of 1-imino-3-(2-piperidino-4-imino-2-thiazolin-5-ylidene)isoindoline, there is obtained as the product a metal chelate pigment corresponding to Formula III in which Me is Ni; R is $CH_3$; $R_1$ and $R_2$ are each hydrogen; $R_3$ is iso-$C_3H_9$; N=B is piperidino; and An is Cl.

EXAMPLE 41

A. Proceeding in a manner similar to that described in Example 9, part B above, but substituting 4,5-dipropyl-7-ethoxy-1,3-diiminoisoindoline and 2-morpholino-4-imino-2-thiazoline hydrochloride in equivalent amounts for 1,3-diiminoisoindoline and 2-piperidino-4-imino-2-thiazoline hydrochloride respectively, there is obtained as the product 1-imino-4,5-dipropyl-7-ethoxy-3-(2-morpholino-4-imino-2-thiazolin-5-ylidene)isoindoline hydrochloride.

B. When an equivalent amount of 1-imino-4,5-dipropyl-7-ethoxy-3-(2-morpholino-4-imino-2-thiazolin-5-ylidene)isoindoline in the free-base form is substituted for 1-imino-3-(2-piperidino-4-imino-2-thiazolin-5ylidene)isoindoline in the procedure described in Example 9, part C above, there is obtained as the product a metal chelate pigment corresponding to Formula III in which Me is Ni; R is $OC_2H_5$; $R_1$ is hydrogen; $R_2$ and $R_3$ are each $C_3H_7$; N=B is morpholino; and An is Cl.

EXAMPLE 42

A. Following the procedure described in Example 9, part B above but using equivalent amounts of 5-chloro-4,6,7-trifluoro-1,3-diiminoisoindoline and 2-(2-methylpiperidino)-4-imino-2-thiazoline hydrochloride in place of 1,3-diiminoisoindoline and 2-piperidino-4-imino-2-thiazoline hydrochloride respectively, there is obtained as the product 1-imino-5-chloro-4,6,7-trifluoro-3-[2-(2-methylpiperidino)-4-imino-2-thiazolin-5-ylidene]isoindoline hydrochloride.

B. When an equivalent of 1-imino-5-chloro-4,6,7-trifluoro-3-[2-(2-methylpiperidino)-4-imino-2-thiazolin-5-ylidine]isoindoline in its free-base form is substituted for the 1-imino-3-(2-piperidino-4-imino-2-thiazolin-5-ylidene)isoindoline, in the procedure described in Example 9, part C above, there is obtained as the product a metal chelate pigment corresponding to Formula III in which Me is Ni; R, $R_1$ and $R_3$ are each F; $R_2$ is Cl; N=B is 2—(CH$_3$)—C$_5H_9$N; and An is Cl.

EXAMPLE 43

A. When equivalent amounts of 4,5,6,7-trimethoxy-1,3-diiminoisoindoline and 2-(3-ethylpyrrolidino)-4-imino-2-thiazoline hydrochloride are substituted for the 1,3-diiminoisoindoline and 2-piperidino-4-imino-2-thiazoline hydrochloride respectively, in the procedure described in Example 9, part C above, there is obtained as the product 1-imino-4,5,7-trimethoxy-3-[2-(3-ethylpyrrolidino)-4-imino-2-thiazolin-5-ylidene]isoindoline hydrochloride.

B. Following the procedure described in Example 9, part C above but using an equivalent amount of 1-imino-4,5,7-trimethoxy-3-[2-(3-ethylpyrrolidino)-4-imino-2-thiazolin-5-ylidene]isoindoline in its free-base form in place of 1-imino-3-(2-piperidino-4-imino-2-thiazolin-5-ylidene)isoindoline, there is obtained as the product a metal chelate pigment corresponding to Formula III in which Me is Ni; R, $R_2$ and $R_3$ are each OCH$_3$; $R_1$ is hydrogen; N=B is 2-($C_2H_5$)$C_4H_7$N; and An is Cl.

EXAMPLE 44

A. Proceeding in a manner similar to that described above in Example 10, part A, but substituting equivalent amounts of 4-bromo-6-methyl-4,5,6,7-tetrahydro-1,3-diiminoisoindoline and 2-(3-methylmorpholino)-4-imino-2-thiazoline hydrochloride for 4,5,6,7-tetrahydro-1,3-diiminoisoindoline and 2,4-diiminothiazolidine hydrochloride respectively, there is obtained as the product 1-imino-4-bromo-6-methyl-4,5,6,7-tetrahydro-3-[2-(3-methylmorpholino)-4-imino-2-thiazolin-5-ylidene]isoindoline.

B. When an equivalent amount of 1-imino-4-bromo-6-methyl-4,5,6,7-tetrahydro-3-[2-(3-methylmorpholino)-4-imino-2-thiazolin-5-ylidene]isoindoline is substituted for 1-imino-4,5,6,7-tetrahydro-3-(2,4-diimino-5-thiazolidinylidene)isoindoline in the procedure described in Example 10, part B above, there is obtained as the product a metal chelate pigment corresponding to Formula V in which Me is Ni; $R_1$ is $CH_3$; $R_3$ is Br; R and $R_2$ are each hydrogen; N=B is 2—$(CH_3)C_4H_7NO$; and An is Cl.

EXAMPLE 45

A. When an equivalent amount of 4,5,6,7-tetraphenyl-1,3-diiminoisoindoline is substituted for the 1,3-diimino-4,5,6,7-tetrachloroisoindoline in the procedure described in Example 3, part A above, there is obtained as the product 1-imino-4,5,6,7-tetraphenyl-3-(2,4-diimino-5-thiazolidinylidene)isoindoline acetate.

B. Following the procedure described in Example 3, part B above but using an equivalent amount of 1-imino-4,5,6,7-tetraphenyl-3-(2,4-diimino-5-thiazolidinylidene)isoindoline acetate in place of 1-imino-4,5,6,7-tetrachloro-3-(2,4-diimino-5-thiazolidinylidene)isoindoline acetate, there is obtained as the product a metal chelate pigment corresponding to Formula II in which Me is Ni; R, $R_1$, $R_2$ and $R_3$ are each $C_6H_5$; Z is NH; and An is Cl.

EXAMPLE 46

This example is representative of one of the procedures employed for the evaluation of the novel pigments of this invention as coloring agents for coating compositions.

A mixture of two parts of the novel pigment obtained in Example 1, part C above, seven parts of an acrylic resin, four parts of xylol and 20 parts of one-sixteenth inch diameter steel balls was charged into a container which was placed in a mechanical shaker. Shaking was effected for one hour. The container was removed from the shaker and to the mixture there was added an additional 17 parts of the acrylic resin and an additional 10 parts of xylol. The container was again placed in the shaker and shaking was effected for 15 minutes longer. The steel balls were removed from the mixture and portions of the composition, which contained approximately 5 percent pigment, were coated on foil-covered paper. The cured acrylic coating was completely transparent and was of a pleasing blue-red shade. The coating was then tested for light-fastness under accelerated conditions by exposing the coated foil-covered specimens to radiation from a carbon arc in a standard light-fast testing apparatus. After 300 hours of continuous exposure, there was no observable loss in strength or shade.

EXAMPLE 47

The novel pigments of this invention were evaluated for use in preparing coating compositions suitable for outdoor exposure, such as automobile finishes. Representative of the method employed is the following description of the preparation and testing of a "metallic" automobile finish.

A pigment base was prepared by subjecting a mixture of 15.7 parts of the chelate pigment from Example 1, part C above, and 16.2 parts of acrylic resin dissolved in 24.6 parts of xylol to attrition in a steel ball mill (one-half inch balls) for 48 hours. To the milled mixture there was then added an additional 4.3 parts of acrylic resin dissolved in 26.2 parts of xylol. The pigment base, which contained 18 percent pigment was incorporated in a coating composition containing 7.7 parts of the pigment base, 3.3 parts of a 30 percent aluminum paste, 19.5 parts of acrylic resin, 15.2 parts of a melamine resin, 1.3 parts of butanol and 35 parts of xylol. The resultant composition was sprayed onto primed 4 × 12 inch steel test panels and the coated panels were then placed in a curing oven at 300° F for 30 minutes. There was thus produced a pleasing blue-red transparent and glossy metallic finish on the test panels.

The coated panels were then tested by outdoor exposure in Florida and under desert sun in Arizona. After 12 months of this continuous exposure there was essentially no perceptible change in the hue, brightness and strength of the pigment.

EXAMPLE 48

A. To 140 parts of 2-ethoxyethanol stirred at 100° C under an atmosphere of nitrogen there was added 8.6 parts of 60 percent active solid sodium sulfide and the resultant solution was filtered to remove undissolved material. The filtrate was mixed with 94 parts of dimethylformamide and 11.3 parts of 3,6-dimethoxyphthalonitrile and the mixture stirred at 25° C for a period of 1 hour. The reaction mixture was then heated to 95° C over a period of 1 hour, cooled to 25° C and filtered to remove undissolved material which was found to be (4.5 parts) unreacted 3,6-dimethoxyphthalonitrile. The filtrate, which contained approximately 0.04 mole of the sodium salt of 4,7-dimethoxy-1-imino-3-mercaptoisoindoline was stirred and there was added 10.7 parts of 2,4-diiminothiazolidinium benzenesulfonate. Stirring was continued overnight at 25° C. The product which separated was collected by filtration, washed successively with four portions of 12.0 parts each of methyl alcohol and finally dried in vacuo to obtain 4.5 parts of 4,7-dimethoxy-1-imino-3-(2,4-diimino-5-thiazolidinylidene)isoindoline as a red solid which melted at 227°–246° C (dec).

B. To a stirred solution of 1.14 parts of zinc chloride in 37.6 parts of dimethylformamide there was added 4.0 parts of 4,7-dimethoxy-1-imino-3-(2,4-diimino-5-thiazolidinylidene)isoindoline. Stirring was continued overnight at ambient temperature. The product was collected by filtration, washed first with a small volume of fresh dimethylformamide, then with acetone, and was finally dried in vacuo at 50° C to obtain 3.1 parts of the zinc chloride adduct, a reddish-brown solid which consisted of two moles of 4,7-dimethoxy-1-imino-3-(2,4-diimino-5-thiazolidinylidene)isoindoline and one mole of zinc chloride.

Anal. Calcd. for $C_{26}H_{26}N_{10}O_4S_2 \cdot ZnCl_2 \cdot 6H_2O$: C, 36.69; H, 4.50; N, 16.46; S, 7.53; Zn, 7.67; Cl, 8.35. Found: C, 37.77; H, 3.67; N, 16.16; S, 7.77; Zn, 6.83; Cl, 8.10.

C. To a stirred solution of 0.86 parts of nickel (II) chloride hexahydrate in 28.3 parts of dimethylformamide there was added at 25° C 2.9 parts of the zinc chloride adduct of 4,7-dimethoxy-1-imino-3-(2,4-diimino-5-thiazolidinylidene)isoindoline from B. The reaction mixture was heated to 100° C during a period of 1 hour and maintained at 98°–100° C for a period of 3 hours. The suspended reddish-brown solid present in the reaction mixture was then collected by filtration at 100° C, washed with warm dimethylformamide, then with water and finally dried in vacuo at 80° C to obtain 1.8 parts of the dark reddish-brown nickel chelate pigment represented by Formula II where Me is Ni; Z is NH; R and R$_3$ are each OCH$_3$; R$_1$ and R$_2$ are each hydrogen; and An is Cl.

Anal. Calcd. for C$_{26}$H$_{23}$N$_9$NiO$_4$S$_2$ . HCl . 3H$_2$O: C, 42.26; H, 4.09; N, 17.06; S, 8.68; Ni, 7.95; Cl, 4.80. Found: C, 41.97; H, 3.90; N, 15.16; S, 5.16; N;, 8.81; Cl, 5.29.

The thus obtained pigment was incorporated into an acrylic coating formulation according to the procedure described in Example 46 above. When applied over foil-covered paper a pleasing transparent brown coating was obtained. When tested for light-fastness under accelerated conditions by exposing the coated foil-covered specimen to radiation from a carbon arc in a standard light-fast testing apparatus, there was no observable loss in strength or shade after 380 hours of continuous exposure.

EXAMPLE 49

A. When an equivalent amount of 5,6-diphenyl-1,3-diiminoisoindoline is substituted for the 1,3-diiminoisoindoline used in the procedure described in Example 1, part A above, there is obtained as the product 1-imino-5,6-diphenyl-3-(2,4-diimino-5-thiazolidinylidene)isoindoline.

B. Following the procedure described in Example 7 above but using an equivalent amount of 1-imino-5,6-diphenyl-3-(2,4-diimino-5-thiazolidinylidene)isoindoline in place of 1-imino-3-(2,4-diimino-5-thiazolidinylidene)isoindoline, there is obtained as the product a metal chelate pigment corresponding to Formula II in which Me is Cu; Z is NH; R$_1$ and R$_2$ are each C$_6$H$_5$; R and R$_3$ are hydrogen; and An is Cl.

EXAMPLE 50

A. When an equivalent amount of 5-phenoxy-1,3-diiminoisoindoline is substituted for the 1,3-diiminoisoindoline in the procedure described in Example 4, part A above, there is obtained as the product 1-imino-5-phenoxy-3-(2-oxo-4-imino-5-thiazolidinylidene)isoindoline.

B. Following the procedure described in Example 4, part B above but using an equivalent amount of 1-imino-5-phenoxy-3-(2-oxo-4-imino-5-thiazolidinylidene)isoindoline in place of 1-imino-3-(2-oxo-4-imino-5-thiazolidinylidene)isoindoline, there is obtained as the product a metal chelate pigment corresponding to Formula II in which Me is Ni; R$_2$ is OC$_6$H$_5$; R, R$_1$ and R$_3$ are each hydrogen; Z is O; and An is OH.

EXAMPLE 51

A. Proceeding in a manner similar to that described above in Example 3, part A but substituting an equivalent amount of 6,7-dichloro-1,3-diiminoisoindoline for the 1,3-diimino-4,5,6,7-tetrachloroisoindoline used in that example, there is obtained 1-imino-6,7-dichloro-3-(2,4-diimino-5-thiazolidinylidene)isoindoline acetate.

B. When an equivalent amount of 1-imino-6,7-dichloro-3-(2,4-diimino-5-thiazolidinylidene)isoindoline acetate is substituted for the 1-imino-4,5,6,7-tetrachloro-3-(2,4-diimino-5-thiazolidinylidene)isoindoline acetate in the procedure described in Example 3, part B above, there is obtained as the product a metal chelate pigment corresponding to Formula II in which Me is Ni; Z is NH; R and R$_1$ are each Cl; R$_2$ and R$_3$ are each hydrogen; and An is Cl.

EXAMPLE 52

A. Proceeding in a manner similar to that described above in Example 4, part A, but substituting an equivalent amount of 5-methoxy-1,3-diiminoisoindoline for 1,3-diiminoisoindoline, there is obtained as the product 1-imino-5-methoxy-3-(2-oxo-4-imino-5-thiazolidinylidene)isoindoline.

B. When an equivalent amount of 1-imino-5-methoxy-3-(2-oxo-4-imino-5-thiazolidinylidene)isoindoline is substituted for 1-imino-3-(2,4-diimino-5-thiazolidinylidene)isoindoline in the procedure described in Example 8 above, there is obtained as the product a metal chelate pigment corresponding to Formula II in which Me is Co; R$_2$ is OCH$_3$; R, R$_1$ and R$_3$ are each hydrogen; Z is O; and An is Cl.

EXAMPLE 53

A. Proceeding in a manner similar to that described above in Example 3, part A, but substituting an equivalent amount of 5-(2', 5'-dimethoxyphenyl)-1,3-diiminoisoindoline for 1,3-diimino-4,5,6,7-tetrachloroisoindoline, there is obtained as the product 1-imino-5-(2', 5'-dimethoxyphenyl)-3-(2,4-diimino-5-thiazolidinylidene)isoindoline acetate.

B. Following the procedure described in Example 3, part B above, but using an equivalent amount of 1-imino-5-(2', 5'-dimethoxyphenyl)-3-(2,4-diimino-5-thiazolidinylidene)isoindoline in the free-base form in place of 1-imino-4,5,6,7-tetrachloro-3-(2,4-diimino-5-thiazolidinylidene)isoindoline, there is obtained as the product a metal chelate pigment corresponding to Formula II in which Me is Ni; R$_2$ is 2,5-(OCH$_3$)$_2$C$_6$H$_3$; R, R$_1$ and R$_3$ are each hydrogen; Z is NH; and An is Cl.

EXAMPLE 54

A. Proceeding in a manner similar to that described above in Example 4, part A, but substituting an equivalent amount of 5-chloro-1,3-diiminoisoindoline for 1,3-diiminoisoindoline, there is obtained as the product 1-imino-5-chloro-3-(2-oxo-4-imino-5-thiazolidinylidene)isoindoline.

B. When an equivalent amount of 1-imino-5-chloro-3-(2-oxo-4-imino-5-thiazolidinylidene)isoindoline is substituted for 1-imino-3-(2,4-diimino-5-thiazolidinylidene)isoindoline in the procedure described in Example 8 above, there is obtained as the product a metal chelate pigment corresponding to Formula II in which Me is Co; R$_2$ is Cl; R, R$_1$ and R$_3$ are each hydrogen; Z is O; and An is Cl.

EXAMPLE 55

A. When an equivalent amount of 7-chloro-1,3-diiminoisoindoline is substituted for the 1,3-diiminoisoindoline in the procedure described in Example 4, part A above, there is obtained as the product 1-imino-7-chloro-3-(2-oxo-4-imino-5-thiazolidinylidene)isoindoline.

B. Following the procedure described in Example 4, part B above but using an equivalent amount of 1-imino-7-chloro-3-(2-oxo-4-imino-5-thiazolidinylidene)isoindoline in place of 1-imino-3-(2-oxo-4-imino-5-thiazolidinylidene)isoindoline, there is obtained as the product a metal chelate pigment corresponding to Formula II in which Me is Ni; R is Cl; R$_1$, R$_2$ and R$_3$ are each hydrogen; Z is O; and An is OH.

We claim:
1. A compound of the formula

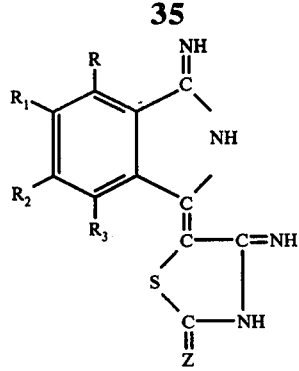

in which R, $R_1$, $R_2$ and $R_3$ are the same or different and are selected from the class consisting of hydrogen, alkyl having 1 to 3 carbon atoms, alkoxy having 1 to 3 carbon atoms, halo, trifluoromethyl, phenyl and phenyl substituted by alkyl having 1 to 3 carbon atoms, alkoxy having 1 to 3 carbon atoms and halogen; and Z is NH, O or S.

2. The compound according to claim 1 wherein R, $R_1$, $R_2$ and $R_3$ are each hydrogen and Z is NH.

3. The compound according to claim 1 wherein R, $R_1$, $R_2$ and $R_3$ are each chlorine and Z is NH.

4. The compound according to claim 1 wherein R and $R_3$ are each methoxy; $R_1$ and $R_2$ are each hydrogen; and Z is NH.

5. The compound according to claim 1 wherein R, $R_1$, $R_2$ and $R_3$ are each hydrogen and Z is O.

6. A compound of the formula

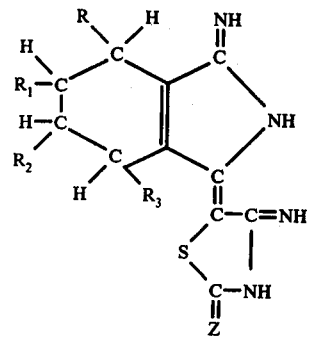

in which R, $R_1$, $R_2$ and $R_3$ are the same or different and are selected from the class consisting of hydrogen, alkyl having 1 to 3 carbon atoms, alkoxy having 1 to 3 carbon atoms, halo, trifluoromethyl, phenyl and phenyl substituted by alkyl having 1 to 3 carbon atoms, alkoxy having 1 to 3 carbon atoms and halogen; and Z is NH, O or S.

7. The compound according to claim 6 wherein R, $R_1$, $R_2$ and $R_3$ are each hydrogen; and Z is NH.

* * * * *

UNITED STATES PATENT AND TRADEMARK OFFICE
CERTIFICATE OF CORRECTION

PATENT NO. : 3,993,658

DATED : November 23, 1976

INVENTOR(S) : Nathan N. Crounse and Nicholas A. Ambrosiano

It is certified that error appears in the above-identified patent and that said Letters Patent are hereby corrected as shown below:

Column 2, lines 20-21, "(lower-alkyl)-(-lower-alkyl)-amino" should read -- (lower-alkyl)-(phenyl-lower-alkyl)amino --.

Column 5 under the formula at lines 23-45, insert -- Formula VI --.

Column 6, line 18, after "phenylamino" insert a comma.

Column 6, in Formula VII,

" 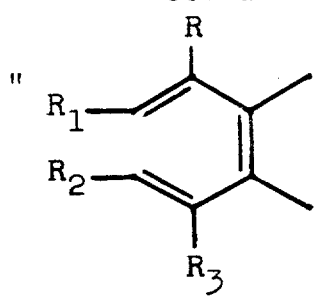 " should read -- 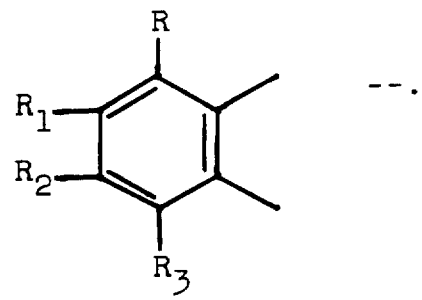 --.

Column 8, in Formula VI,

" 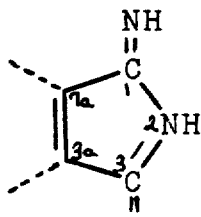 " should read -- 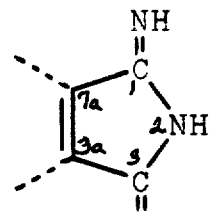 --.

UNITED STATES PATENT AND TRADEMARK OFFICE
CERTIFICATE OF CORRECTION

PATENT NO. : 3,993,658

DATED : November 23, 1976

INVENTOR(S) : Nathan N. Crounse and Nicholas A. Ambrosiano

It is certified that error appears in the above-identified patent and that said Letters Patent are hereby corrected as shown below:

Column 9, line 48, change "amino:" to read -- amino; --.

Column 11, line 17, "2methoxyethanol" should read -- 2-methoxyethanol --.

Column 15, line 22, "VI" should read -- the --.

Column 15, line 23, "V Vi" should read -- V, VI --.

Signed and Sealed this

Seventh Day of May 1985

[SEAL]

Attest:

DONALD J. QUIGG

Attesting Officer   Acting Commissioner of Patents and Trademarks